US005739022A

United States Patent [19]

Burstyn et al.

[11] Patent Number: 5,739,022

[45] Date of Patent: Apr. 14, 1998

[54] COPPER(II) NUCLEASE COMPOUNDS, COMPOSITIONS, AND KITS

[75] Inventors: Judith N. Burstyn; Eric L. Hegg, both of Madison, Wis.; Kim A. Deal, St. Louis, Mo.

[73] Assignee: Wisconsin Alumni Research Foundation, Madison, Wis.

[21] Appl. No.: 293,237

[22] Filed: Aug. 18, 1994

[51] Int. Cl.[6] .............................. C12N 9/99; C07H 21/00

[52] U.S. Cl. .............................. 435/184; 435/6; 435/195; 435/196; 435/199; 436/2; 436/73; 436/80; 436/91; 436/106; 436/145; 514/1; 514/183; 514/499; 514/740; 514/742; 540/1; 549/200; 549/346

[58] Field of Search .............................. 435/6, 195, 196, 435/199, 184; 436/2, 73, 80, 91, 106, 145; 514/1, 183, 499, 740, 742; 540/1; 549/200, 346; 568/300, 18; 935/1, 16, 17, 88; 536/25.3

[56] References Cited

U.S. PATENT DOCUMENTS

| 5,247,075 | 9/1993 | Parker et al. | 540/465 |
|---|---|---|---|
| 5,248,600 | 9/1993 | Topal et al. | 435/91.53 |

OTHER PUBLICATIONS

M. V. Martinez-Diaz et al., *Inorganica Chimica Acta*, vol. 219, No. 1-2, (1994) pp. 85–92.

F. I. Bel'skii et al., *Russian Chemical Reviews*, vol. 61, No. 2, (1992) pp. 415–455 (Translated from *Uspekhi Khimii*, vol. 61, (1992) pp. 415–455).

R. W. Hay et al., *Transition Metal Chemistry*, vol. 17, No. 2, (1992) pp. 81–83.

A. Bianchi et al., *Coordination Chemistry Reviews*, vol. 110, No. 1., (1991) pp. 17–113.

P. G. Graham et al., *Inorganica Chimica Acta*, vol. 178, No. 2, (1990) pp. 227–232.

D. G. Fortier et al., *J. Chem. Soc. Dalton Trans.*, No. 1, (1991) pp. 101–109.

R. Bhula et al., *Coordination Chemistry Reviews*, vol. 91, (1988) pp. 89–213.

P. M. Schaber et al., *Inorganic Chemistry*, vol. 27, No. 9, (1988) pp. 1641–1646.

P. Chaudhuri et al., *Progress in Inorganic Chemistry*, vol. 35, (1987) pp. 329–436.

A. D. Beveridge et al., *J. Chem. Soc. Dalton Trans.*, No. 2, (1987) pp. 373–377.

E. Kimura et al., *Inorganic Chemistry*, vol. 25, No. 22, (1986) pp. 3883–3886.

P. Chaudhuri et al., *Inorganic Chemistry*, vol. 25, No. 16, (1986) pp. 2818–2824.

K. Wieghardt et al., *Inorganic Chemistry*, vol. 24, No. 8, (1985) pp. 1230–1235.

H. Gampp, *Inorganic Chemistry*, vol. 23, No. 18, (1984) pp. 2793–2798.

K. Wieghardt et al., *Zeitschrift Fur Naturforschung Section B–A Journal of Chemical Sciences*, vol. 38, No. 1, (1983) pp. 81–89.

A. E. Martin et al., *Journal of Organic Chemistry*, vol. 47, No. 3, (1982) pp. 412–415.

B. J. Hathaway, *Coordination Chemistry Reviews*, vol. 41, No. 1–4, (1982) pp. 423–487.

P. G. Graham et al., *Australian Journal of Chemistry*, vol. 34, No. 2, (1981) pp. 291–300.

Burstyn, J. N. and Deal, K. A., *Inorganic Chemistry*, vol. 32 (1993) pp. 3585–3586, published Aug. 18, 1993.

Deal, K. A. and Burstyn, J. N., *Mechanistic Studies of Phosphodiester Hydrolysis With a Macrocyclic Copper(II) Catalyst*, Paper given at American Chemical Society meeting, Denver, Colorado in Apr. 1993 and abstract, (1 page).

(List continued on next page.)

*Primary Examiner*—Ardin H. Marschel

*Attorney, Agent, or Firm*—Teresa J. Welch; Stroud, Stroud, Willink, Thompson & Howard

[57] ABSTRACT

A method is provided for nonoxidatively cleaving the phosphorus-oxygen linkage of nucleic acids and certain anticholinesterases such as insecticides using a macrocyclic copper(II) complex. A composition suited for such cleavage is also provided.

30 Claims, 11 Drawing Sheets

OTHER PUBLICATIONS

Deal, K. A. and Burstyn, J. N., *Copper(II) Complexes of Cyclic Triamines as Promoters of Phosphodiester Hydrolysis*, Poster Sesssion given at American Chemical Society meeting in Milwaukee, Wisconsin in Jun. 1992, (15 pages) and abstract, (1 page).
Deal, K. A. and Burstyn, J. N. , *Metal Promoted Phosphodiester Hydrolysis Using the Triazacyclononane Ligand*, Poster Session given at American Chemical Society meeting in San Francisco, California in Apr. 1992, (13 pages) and abstract, (1 page).
Abstracts of Papers of the Am. Chem. Soc., vol. 205, (1993) March Issue, p. 485, INOR.
Morrow, J. R. et al., *Inorg. Chem.*, vol. 31, No. 1, (1992) pp. 16–20.
Morrow, J. R. et al., *J. Am. Chem. Soc.*, vol. 114, No. 5, (1992) pp. 1903–1905.
Shelton, M. M. et al., *Inorg. Chem*, vol. 30, No. 23, (1991) pp. 4295–4299.
Breslow, R. et al., *Proc. Natl. Acad. Sci. USA*, vol. 88, (May 1991) pp. 4080–4083.
Modak, A. S. et al., *J. Am. Chem. Soc.*, vol. 113, No. 1, (1991) PP. 283–291.
Kimura, E. et al., *J. Am. Chem. Soc.*, vol. 112, No. 15, (1990) pp. 5805–5811.
Stern, M. K. et al., *J. Am. Chem. Soc.*, vol. 112, No. 13, (1990) pp. 5357–5359.
Murakawa, G. J. et al., *Nucleic Acids Research*, vol. 17, No. 13, (1989) pp. 5361–5375.
Bevilacqua, A. et al., *Inorg. Chem.*, vol. 26, No. 16, (1987) pp. 2699–2706.
Scheller–Krattiger, V. et al., *Inorganic Chemistry*, vol. 25, No. 15, (1986) pp. 2628–2634.
Bereman, R. D. et al., *Inorganic Chemistry*, vol. 18, No. 11, (1979) pp. 3122–3125.
Zompa, L. J., *Inorganic Chemistry*, vol. 17, No. 9, (1978) pp. 2531–2536.
Nonoyama, M., *Transition Met. Chem.*, vol. 1, (1976) pp. 70–74.
Bashkin, J. K. et al., *J. Am. Chem. Soc.*, vol. 116, No. 13., (1994) pp. 5981–5982.
Bashkin, J. K. et al., *J. Chem. Soc. Dalton Trans.*, (1993) pp. 3631–3632.
Westheimer, F. H., *Science*, 235 (1987) pp. 1173–1178.
Hendry, P. and Sargeson, A. M., *Progress in Inorganic Biochemistry: Bioinorganic Chemistry*, 38 (1990) pp. 201–258.
Kirby, A. J. and Younas, M. J., *J. Chem. Soc.*, B, (1970) pp. 510–513.
Hendry, P. and Sargeson, A. M., *J. Amer. Chem. Soc.*, 111 (1989) pp. 2521–2527.
Chin, J. et al., *J. Amer. Chem Soc.*, 111 (1989) pp. 186–190.
Morrow, J. R. and Torgler, W. C., *Inorg. Chem.*, 27 (1988) pp. 3387–3394.
DeRosch, M. A. and Trogler, W. C., *Inorg. Chem.*, 29 (1990) pp. 2409–2416.
Chin, J. and Zou, X., *J. Am. Chem. Soc.*, 110 (1988) pp. 223–225.
Koike, T. and Kimura, E., *J. Am. Chem. Soc.*, 113 (1991) pp. 8935–8941.
Chin, J. and Zou, X., *Can. J. Chem.*, 65 (1987) pp. 1882–1884.
Matsumoto, Y. and Komiyama, M., *J. Chem. Soc., Chem Commun.*, (1990) pp. 1050–1051.
Stern, M. K. et al., *J. Am. Chem. Soc.*, 112 (1990) pp. 5357–5359.
Modak, A. S. et al., *J. Am. Chem. Soc.*, 113 (1991) pp. 283–291.
Shelton, V. M. and Morrow, J. R., *Inorg. Chem.*, 30 (1991) pp. 4295–4299.
Morrow, J. R. et al., *J. Am. Chem. Soc.*, 114 (1992) pp. 1903–1905.
Kolasa, K. A. et al., *Inorg. Chem.*, 32 (1993) pp. 3983–3984.
Basile et al., *J. Amer. Chem. Soc.*, 109 (1987) pp. 7550–7551.
Morrow et al., *Inorg. Chim. Acta*, 195 (1992) pp. 245–248.
Schwindinger et al., *Inorg. Chem.*, 19 (1980) pp. 1379–1381.
Smith et al., *J. Am. Chem. Soc.*, 100 (1978) pp. 3539–3544.
Koyama et al., *Bull. Chem. Soc. Jap.*, 45 (1972) pp. 481–484.
Richman et al., *J. Am. Chem. Soc.*, 96 (1974) pp. 2268–2270.
Searle et al., *Aust. J. Chem.*, 37 (1984) pp. 959–970.
Rabhofer et al., *Liebigs Ann. Chem.*, 916 (1976) pp. 916–923.
V. J. Thöm, M. S. Shaikjee, and R. D. Hancock, *Inorg. Chem.*, 25 (1986) pp. 2992–3000.
E. K. Barefield and F. Wagner, *Inorg. Chem.*, 12 (1973) pp. 2435–2439.
Chaudhuri, et al., *J. Chem. Soc. Dalton Trans.*, (1990) pp. 1597–1605.
Chaudhuri, et al., *Angew. Chem. Int. Ed. Entl.*, 24 (1985) pp. 57–59.
Martell et al., *Critical Stability Constants*, Plenum Press, New York, (1977) vol. 3, p. 183.
A. E. Martin et al., *J. Org. Chem.*, 47 (1982) pp. 412–415.
Larock, Richard G., *Comprehensive Organic Transformations:* A Guide to Functional Group Preparations, VCH Publishers, Inc., New York, New York (1989) pp. 432–434.
Corey, S., *Tet. Lett.*, (1975) pp. 2647–2650.
R. P. Hertzberg and P. B. Dervan, *Biochem.*, 23 (1984) pp. 3934–3945.
Keck and Lippard, *Tet. Lett.*, 34 (1993) pp. 1415–1416.
E. C. Long and J. K. Barton, *Acc. Chem. Res.*, 23 (1990) pp. 271–273.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: both
( D ) TOPOLOGY: linear ( i x ) FEATURE:
( A ) NAME/KEY: stem_loop
( B ) LOCATION: 1..20
( D ) OTHER INFORMATION: /note="Nucleotides 1-8 base pair with nucleotides 20-13. Nucleotides 9-12 form a single- stranded loop."

( x i ) SEQUENCE DESCRIPTION: SEQ ID NO:1:

UCCCCCUCUU CGGAGGGGGA 20

COPPER(II) NUCLEASE COMPOUNDS, COMPOSITIONS, AND KITS

TECHNICAL FIELD

The invention relates generally to a method for cleaving nucleic acids using a synthetic chemical nuclease, and more specifically, for cleaving the phosphorus-oxygen linkages of DNA or RNA using a macrocyclic copper(II) complex at near-physiological pH.

BACKGROUND OF THE INVENTION

There has recently been considerable interest in the development of chemical nucleases, i.e., synthetic nonenzymatic reagents that can recognize and cleave specific nucleic acid structures or sequences. Because of the intimate role of metal ions in enzymatic cleavage reactions, research has turned to developing metal ions or metal ion complexes that can cleave nucleic acids.

Cleavage of DNA may occur by oxidative or hydrolytic reactions. For RNA, cleavage is achieved by oxidative, hydrolytic or transesterification mechanisms. Given the latter additional cleavage mechanism for RNA, it is clear that methods for cleavage of the phosphodiester backbone of DNA are more limited.

Because of the intrinsic stability of the phosphodiester backbone to hydrolysis, considerable emphasis, however, has focused on oxidative and transesterification cleavage. Oxidative cleavage as it is presently practiced is not compatible with living cells, i.e., it cannot be carried out in vivo. On the other hand, hydrolysis of nucleic acids requires the attack of a water molecule or hydroxide ion on the negatively charged phosphodiester bond, a bimolecular reaction that is disfavored because of electrostatic interactions. (Westheimer, F. H., *Science*, 235 (1987) 1173–1178). Nonetheless, hydrolytic chemistry is intrinsically compatible with living cells.

Complexes that hydrolytically cleave RNA and DNA, preferably catalytically, thus, would be the preferred method for cleavage, because hydrolysis would not require redox cofactors to mediate the chemistry nor would highly reactive oxene or oxy radical species (often found in oxidative cleavage) be generated. In addition, hydrolytic manipulation of nucleic acid polymers would generate fragments that are chemically competent for ligation to other oligonucleotides by routine enzymatic reactions.

To identify possible mechanisms by which metal ions promote phosphodiester hydrolysis, certain model compounds that are activated phosphodiesters have been used to study the hydrolysis reaction because these compounds hydrolyze more readily than DNA or RNA and the reactions can be followed easily by visible spectroscopy. (Hendry, P. and Sargeson, A. M., *Progress in Inorganic Biochemistry: Bioinorganic Chemistry*, 38 (1990) 201–258.) One such compound is bis(p-nitrophenyl)phosphate (BNPP). BNPP has a half life of over four months at 100° C. in 0.1M base, or a half life of 73 years at 50° C. and neutral pH, compared to an estimated 200 million years for DNA. (Kirby, A. J. and Younas, M. J., *J. Chem. Soc.*, B, (1970) 510–513.) Because of the shorter half-life of BNPP, the hydrolysis proceeds more rapidly than for DNA. Although BNPP serves as a good indicator of whether a metal complex can catalytically hydrolyze a phosphodiester bond in a small molecule, there is no certainty that such a catalyst can also hydrolyze phosphodiester bonds in the macromolecules of DNA and RNA, particularly double-stranded DNA.

Studies of metal-promoted hydrolysis of activated phosphodiesters have been reported. See, for example, Hendry, P. and Sargeson, A. M., *J. Amer. Chem. Soc.*, 111 (1989) 2521–2527 (complexes of Co(III) and Ir(III)); Chin, J. et al., *J. Amer. Chem Soc.*, 111 (1989) 186–190 (pseudolabile cis-Co(III)$N_4(H_2O)_2$ complexes, where $N_4$ is one of a number of facially chelating tetraamine ligands); Morrow, J. R. and Trogler, W. C., *Inorg. Chem.*, 27 (1988) 3387–3394 ($Cu(bpy)^{2+}$ where bpy=2,2'-bipyridine); DeRosch, M. A. and Trogler, W. C., *Inorg. Chem.*, 29 (1990) 2409–2416(Zn $[12]aneN_3^{2+}$ and $Zn(cyclen)^{2+}$ and $Ni(cyclen)^{2+}$ where $[12]aneN_3$ is 1,4,7-triazacyclododecane and cyclen=1,4,7,10-tetraazacyclododecane); Chin, J. and Zou, X., *J. Am. Chem. Soc.*, 110 (1988) 223–225, ($[Co(en)_2(NH_3)(OH)]^{2+}$, $[Co(en)_2(OH_2)(OH)]^{2+}$$[Co(trien)(OH_2)(OH)]^{2+}$, $[Co(dien)(OH_2)(OH)]^{2+}$, where dien=diethylenetriamine, trien=triethylenetetraamine and en=ethylenediamine); Koike, T. and Kimura, E., *J. Am. Chem. Soc.*, 113 (1991) 8935–8941 ($Zn[12]aneN_3^{2+}$, $Zn[12]aneN_4^{2+}$); Chin, J. and Zou, X., *Can. J. Chem.*, 65 (1987) 1882–1884, ($[Co(trien)(OH_2)(OH)]^{2+}$, $[Co(en)_2(NH_3)(OH)]^{2+}$ and $Zn^{2+}$).

Two important conclusions have emerged from these model compound studies that bear on the design of potential hydrolytic catalysts: (1) the metal ion must have two labile coordination sites in order to bind both the phosphodiester substrate and a water molecule, and (2) the metal ion must be a strong Lewis acid in order to facilitate deprotonation of the coordinated water to generate the hydroxide nucleophile.

Some hydrolytic cleavage studies of RNA have been reported for transition metal complexes. There is evidence that the cobalt complex, $Co(trien)(H_2O)_2^{3+}$, is capable of hydrolyzing the dinucleotide adenylyl(3'-5') adenosine (ApA) (Matsumoto, Y. and Komiyama, M., *J. Chem. Soc., Chem Commun.*, (1990) 1050–1051). The copper complexes, $Cu(trpy)^{2+}$ (trpy=2,2', 6', 2"-terpyridine) and $Cu(bpy)^{2+}$ are reported to hydrolyze the RNA oligomer $poly(A)_{12-18}$ (Stern, M. K. et al., *J. Am. Chem. Soc.*, 112 (1990) 5357–5359). The rate of the reaction can be attenuated by covalently linking the bipyridine ligand to a nucleoside (Modak, A. S. et al., *J. Am. Chem. Soc.*, 113 (1991) 283–291). It has also been reported that $Zn([9]aneN_3)^{2+}$, $Zn([12]aneN_3)^{2+}$, and $Zn(cyclam)^{2+}$ ($[9]aneN_3$=1,4,7-triazacyclononane and cyclam=1,4,8,11-tetraazacyclotetradecane) hydrolyze the dinucleotide adenylyl-3'5'-uridine 3'-monophosphate (ApUp) (Shelton, V. M. and Morrow, J. R., *Inorg. Chem.*, 30 (1991) 4295–4299). Additionally, it has been demonstrated, utilizing a macrocyclic Schiff base, that lanthanide metal complexes of $La^{3+}$, $Eu^{3+}$, $Gd^{3+}$, $Tb^{3+}$, and $Lu^{3+}$ are also capable of hydrolyzing the dinucleotide ApUp (Morrow, J. R. et al., *J. Am. Chem. Soc.*, 114 (1992) 1903–1905). These same complexes are not, however, capable of hydrolyzing DNA-RNA hydrids (Kolasa, K. A. et al., *Inorg. Chem.*, 32 (1993) 3983–3984).

Hydrolytic cleavage of DNA has also been reported. Basile et al., *J. Amer. Chem. Soc.*, 109 (1987) 7550–7551, reported DNA hydrolytic cleavage with a metal complex, ($Ru(DIP)_2Macro^{n+}$) (DIP=4,7-diphenyl-1,10-phenanthroline; Macro=4-7-$[(NH_2CH_2CH_2)_2NCH_2CH_2NSO_2C_6H_4]$-1,10-phenanthroline) where the DIP ligands serve to direct the complex to the DNA and the Macro ligand contains chelate arms to bind divalent metals and promote hydrolysis. This hydrolytic cleavage was achieved at pH=8.5 in the presence of $Co^{2+}$, $Cu^{2+}$,$Zn^{2+}$, $Cd^{2+}$ and $Pb^{2+}$. Morrow et al., *Inorg. Chim. Acta*, 195 (1992) 245–248, reported cleavage of DNA by nickel complexes; however, there appeared to be evidence that the cleavage is oxidative. DeRosch et al., *Inorg. Chem.*, 29 (1990) 2409–2416, reported that $M(bpy)^{2+}$ and $M(tren)^{2+}$, (M=Ni (II) or Cu(II)) were generally not effective for nicking supercoiled plasmid DNA; however, $Cu(bpy)^{2+}$ was observed to cleave the plasmid DNA oxidatively.

Use of the chemical nucleases for in vitro or in vivo applications necessitates reactivities at near physiological pH. Despite extensive research efforts and recognition of the limitations of currently available hydrolytically catalytic chemical nucleases, introduction of a synthetic chemical nuclease that can be tailored to cleave DNA or RNA at near neutral pH at a designated site has not occurred. Chemical nucleases, with such properties could extend the capabilities of molecular biology by allowing researchers to target specific sites for cleavage and would enable chemical cleavage to be used to generate clonable DNA fragments.

SUMMARY OF THE INVENTION

The present invention provides a method of nonoxidatively cleaving phosphorus-oxygen linkages in substrate nucleic acids utilizing a synthetic, nonenzymatic metallo-nuclease. The chemical nuclease possesses surprising catalytic properties to provide cleavage rates that are orders of magnitude higher than uncatalyzed reactions. Specifically, the method of nonoxidatively cleaving the phosphorus-oxygen linkage of a substrate which is DNA or RNA comprises the step of cleaving the DNA or RNA phosphorus-oxygen linkages with an effective amount of the following metallo-nuclease of formula (I):

$$L^1—M—L^2_b \quad (I)$$

wherein:

M is a pentacoordinate metal ion;

$L^1$ is tridentate facially chelating ligand which is a heterocycle having 3 heteroatoms and from 6 to 9 carbon atoms within the heterocycle; and $L^2$ is a substitutionally labile ligand disposed around M in cis coordinate positions and b is an integer having of value of 1 or 2.

M is preferably copper(II). The copper(II) ion ($Cu^{2+}$) is pentacoordinate with three of the coordination positions occupied by a tridentate $L^1$ ligand, $L^1$ being preferably a macrocyclic ligand, which is a heterocycle. The remaining two coordination positions are occupied by a substitutionally labile, catalytically acceptable anion $L^2$.

Specifically, $L^1$ is preferably a ligand represented by formula (II):

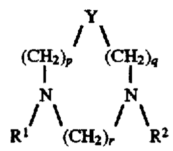

(II)

wherein:

p, q, and r are integers having the values 2 or 3;

$R^1$ and $R^2$ are each independently hydrogen or $C_1$–$C_6$ alkyl; and

Y is oxygen, sulfur or N—$R^3$ wherein $R^3$ is hydrogen, $C_1$–$C_6$ alkyl or I, wherein I is an intercalator moiety. I is preferably a phenanthridine derivative which is ethidium or methidium.

$L^2$ is suitably $X^e$ which is a catalytically acceptable anion, and wherein e is the absolute value of the charge on X and (e b)=2. X is preferably $Br^-$, $Cl^-$, $ClO_4^-$, $CF_3SO_3^-$ or $NO_3$—. The cleaving step occurs in an aqueous medium, and may occur catalytically and/or hydrolytically.

The method of the present invention encompasses the use of the aforementioned copper(II) complex with $L^1$ as the compound of formula (II) wherein Y is N—$R^3$; $R^1$, $R^2$ and $R^3$ are each hydrogen; and p, q and r are each equal to 2, whereby $L^1$ is represented by the formula, $[9]aneN_3$ (nomenclature shorthand explained hereinbelow), and wherein the metallo-nuclease is preferably $Cu([9]aneN_3)Cl_2$.

Also preferred is the use of the aforementioned copper(II) complex, with $L^1$ as the compound of formula (II): (a) wherein Y is N—$R^3$; $R^1$, $R^2$ and $R^3$ are each hydrogen; p equals 3; and q and r are each equal to 2, and $L^1$ is represented by the formula, $[10]aneN_3$; (b) wherein Y is N—$R^3$; $R^1$, $R^2$ and $R^3$ are each hydrogen; p and q equal 3; and r equals 2, and $L^1$ is represented by the formula, $[11]aneN_3$; and (c) wherein Y is N—$R^3$; $R^1$, $R^2$ and $R^3$ are each hydrogen; and p, q and r are each equal to 3, and $L^1$ is represented by the formula, $[12]aneN_3$.

It has been unexpectedly found that the complexes in accordance with the present invention cleave both RNA and DNA, and in an illustrated embodiment are expected to have application to cleave double-stranded DNA. The methods of the present invention overcome previous methods in which cleavage by metal complexes, particularly copper complexes, occurs by oxidation.

Specifically, the method entails coincubation of the aforementioned complexes in accordance with the present invention with substrate DNA or RNA, preferably at near-physiological pH, to hydrolytically cleave the phosphodiester linkage. Catalytic hydrolysis has been observed with 10 turnovers with about $10^3$ rate enhancement for model phosphodiesters.

When the substrate is RNA, the cleaving step of the present invention is conducted at a pH of about 7.0 to about 7.5 and at a temperature of about 25° C. to 37° C. Where the substrate is DNA, the cleaving step is conducted at a pH of about 7.8 to 8.5 and at a temperature of about 25° C. to about 55° C. Cleavage is typically conducted for a reaction period of between about 6 hours and 24 hours. Preferably, where the substrate is RNA and is present at a concentration of 1μM, the amount of the metallo-nuclease complex is at least 0.1 mM, and the cleaving step is conducted at a pH of about 7.2, a temperature of about 37° C. and a reaction period greater than 6 hours. Preferably, where the substrate is DNA and is present at a concentration of 0.05 mg/ml, the amount of the metallo-nuclease is at least 0.1 mM, and the cleaving step of the method of the present invention is conducted at a pH is about 7.8, a temperature of about 50° C., and a reaction period of at least 6 hours.

In another aspect, the present invention is a composition comprising a synthetic nonenzymatic metallo-nuclease represented by the formula (I), described herein, wherein M is $Cu^{2+}$; and $L^2$ is $X^e$ which is catalytically acceptable anion, and wherein e is the absolute value of the charge on X and e times b equals 2, in aqueous solution at a physiologically acceptable pH and ionic strength. $L^1$ is preferably the compound of formula (II), described herein. The composition is present in a catalytic amount so as to cleave the phosphorus-oxygen linkage of DNA and RNA when exposed thereto.

By varying the sigma donor properties of the ligand $L^1$, i.e., by varying the ring size, the heteroatoms, and the substituents on them, rate enhancement may be varied. Specifically, the invention comprehends $Cu([10]aneN_3)X_2$; $Cu([11]aneN_3)X_2$ and $Cu([12]aneN_3)X_2$, wherein X is $Br^-$, $Cl^-$, $ClO_4^-$, $CF_3SO_3^-$ or $NO_3^-$.

The present invention further comprehends a kit for cleaving the phosphorous-oxygen linkages of RNA or DNA with the kit comprising a cleavage incubation composition comprising a copper(II) triazacycloalkane cleaving agent in aqueous solution at a physiologically acceptable pH and ionic strength. Preferably the concentration of the cleaving agent is between 0.1 mM and 10 mM.

The compounds of the inventive compositions also find important application in cleaving, and therefore, decomposing and detoxifying, agents having phosphodiester linkages or derivatives thereof, namely, anticholinesterases such as insecticides. Another aspect of the present invention includes a method of decomposing agents which are anticholinesterases having phosphorous-oxygen linkages, comprising the step of reacting the agents with an effective amount of a complex represented by the formula (I), described herein, and wherein $L^1$ is the compound of formula (II), described herein.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF DRAWING

The preferred exemplary embodiment of the present invention will hereinafter be described in conjunction with the appended drawing wherein like designations refer to like elements throughout and in which:

FIG. 5A' is a representation of the intercalator moiety of FIG. 5A with the moiety bound within a Cu(II) complex in accordance with the present invention;

FIG. 5B' is a representation of the intercalator moiety of FIG. 5B with the moiety bound within the Cu(II) complex in accordance with the present invention;

DETAILED DESCRIPTION OF PREFERRED EMBODIMENT

Figure 1:
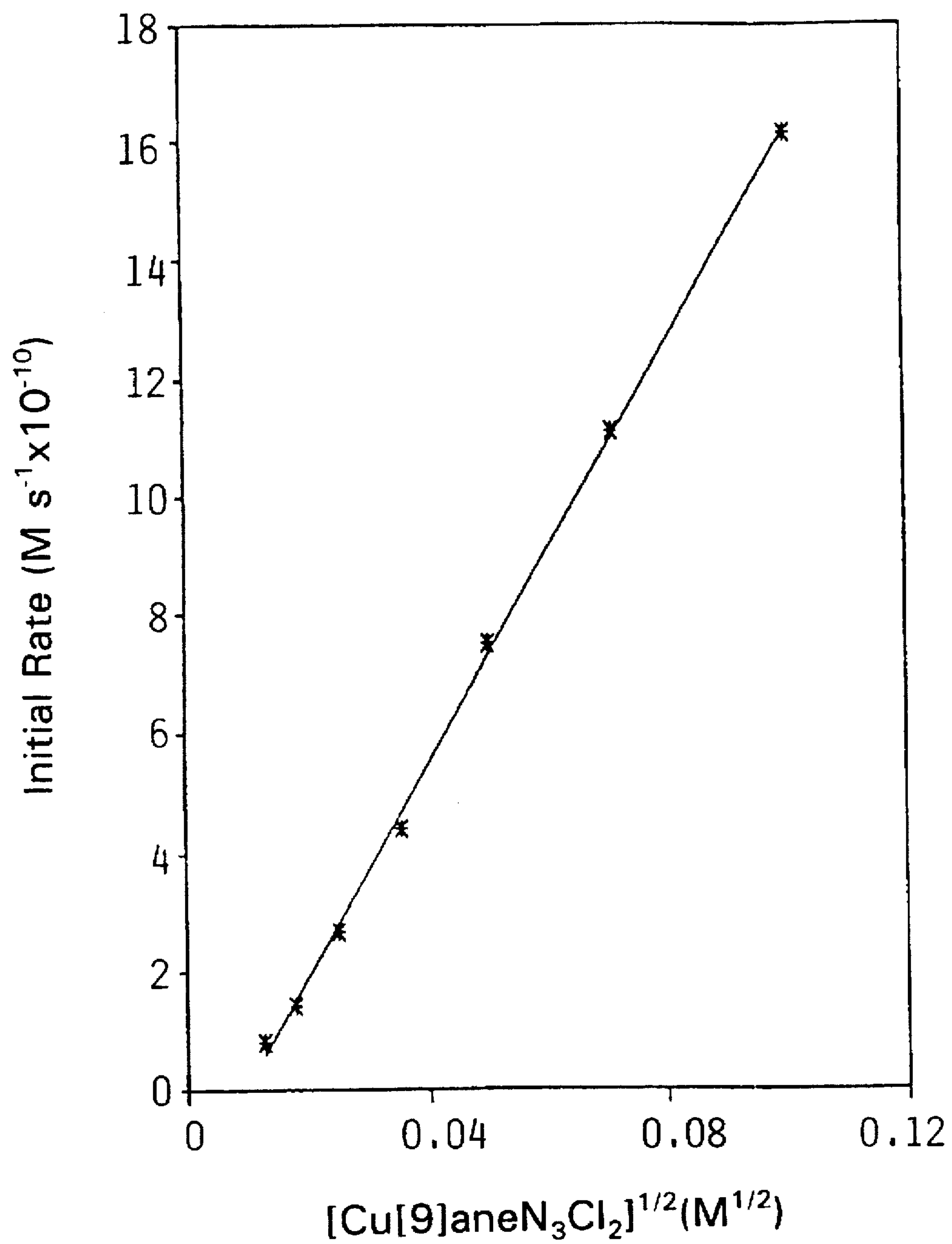
FIG. 1 is a graph of initial reaction rate (in units of $M\ s^{-1} \times 10^{-10}$) v. concentration of the complex of the present invention.

The present invention relates broadly to methods of cleaving nucleic acids utilizing synthetic chemical nucleases. However, the method of the present invention is most particularly adapted for use in catalytically cleaving the phosphorus-oxygen linkages of DNA and RNA. Accordingly, the present invention will now be described in detail with respect to such endeavors; however, those skilled in the art will appreciate that such a description of the invention is meant to be exemplary only and should not be viewed as limitative on the full scope thereof.

In the following description of the method of the invention, process steps are carried out at physiologic temperature (about 37° C.) and atmospheric pressure unless otherwise specified.

As used herein and generally used in the art, the term "facially chelating" refers to a ligand which spans one face of a metal ion, forming an equilateral triangle. The term "heterocycle" or "heterocyclic moiety," as used herein and in the art, refers to a cyclic carbon ring having atoms other than carbon, i.e., heteroatoms, as part of the ring structure. The terms "coordinate" or "coordinated," as used herein and in the art, refers to the bonding of a metal ion to a ligand. The terms "tridentate" or "monodentate," as used herein and in the art, refer to the number of coordinate bonds that a single ligand forms with a metal ion. The term "substitutionally labile" refers to the ease with which a ligand can be substituted with another ligand. The term "catalytically acceptable" with respect to anionic ligands is meant to refer to anions that coordinate to a metal ion in a complex exhibiting catalytic properties. The term "near-physiological pH" refers to a pH range from 7.0 to 8.5, preferably the range from pH=7.2 to 7.8.

In one of its aspects, the invention relates to a method of cleaving phosphorus-oxygen linkages in DNA or RNA utilizing a catalytic amount of the compounds of the formula (I)

$$L^1—M—L^2_b \qquad (I)$$

where M is a pentacoordinate metal ion, preferably $Cu^{2+}$, $L^1$ and $L^2$ are ligands, and b is the number of $L^2$ ligands per compound. Copper(II) being pentacoordinate, has an approximate square pyramidal geometry. $L^1$ is a facially chelating ligand and occupies three of the five coordination positions. The remaining two positions are cis-oriented and occupied by labile ligands, preferably catalytically acceptable anions.

Specifically, $L^1$ is a heterocycle having 3 heteroatoms and from about 6 to 9 carbon atoms within the heterocycle; $L^2$ is $X^e$ which is a catalytically acceptable anion and wherein e is the absolute value of the charge on X and e times b, (e b)=2. Catalytically acceptable anions include $Cl^-$, $Br^-$, $NO_3^-$, $CF_3SO_3^-$ and $ClO_4^-$. These anions are labile in aqueous solution. Preferred among the anions X are $Cl^-$, $Br^-$, and $NO_3^-$ in aqueous solution. In aqueous solutions, these anions will exchange with water rapidly (i.e., at k~$10^9$ $s^{-1}$). Certain of the complexes of the present invention are shock sensitive, therefore appropriate cautions are to be taken during the synthesis and handling of these materials. It is to be particularly noted that although $ClO_4^-$ works well, complexes containing $ClO_4^-$ are potentially explosive.

Preferably, $L^1$ is a ligand of formula (II):

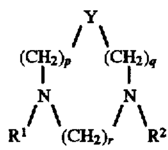

wherein p, q and r are integers with a value of 2 or 3; $R^1$ and $R^2$ are each independently hydrogen or a 1 to 6 carbon alkyl group, i.e., $C_1$ to $C_6$ alkyl; and Y is an oxygen (O), or sulfur (S) or N—$R^3$ wherein $R^3$ is hydrogen, or $C_1$ to $C_6$ alkyl or I which is an intercalator that is a DNA binding group. I is preferably a phenanthridine derivative which is ethidium or methidium.

The compounds of formula (II) are referred to by a shorthand notation "[n]ane$B_l$," where n is the number of total atoms in the heterocyclic ring, B represents the heteroatoms and l the number of heteroatoms. For example, if l=3 and all the heteroatoms are nitrogen, and the number of carbon atoms is 6, the shorthand designation is "[9]ane$N_3$." If there are 9 carbon atoms and 3 nitrogens in the heterocycle, the designation is "[12]ane$N_3$." If the latter compound has an oxygen substituted for one of the nitrogens, the designation is "[12]ane$N_2$O." It is noted that when l=3 and all heteroatoms are nitrogen, the compounds of formula (II) are also referred to as triazacycloalkanes, for example, 1,4,7-triazacyclononane, i.e, [9]ane$N_3$.

Most preferred among the compounds of formula (II) are: [9]ane$N_3$; [10]ane$N_3$; [11]ane$N_3$; [12]ane$N_3$; [9]ane$N_2$O; and $(CH_3)_3$[9]ane$N_3$.

Following the above-described notation for preferred compounds of formula (II), the preferred compounds among those of formula (I) may be expressed by the formula Cu([n]ane$B_l$)$X_2$, where n and $B_1$ have the same meaning as above, and X represents a catalytically acceptable anion with a charge of −1. Specifically, preferred compounds include: Cu([9]ane$N_3$)$Cl_2$; Cu([10]ane$N_3$)$Br_2$; Cu([11]ane$N_3$)$Br_2$; Cu$(CH_3)_3$[9]ane$N_3Cl_2$ and Cu([12]ane$N_3$)$Br_2$. Most preferred is Cu([9]ane$N_3$)$Cl_2$.

The compounds of formula (I) have been found to possess valuable catalytic properties. They catalytically hydrolyze phosphodiester bonds. In particular, it is possible to use the compounds of formula (I) to catalytically hydrolyze the phosphodiester linkages of polynucleotides, namely, DNA and RNA. It has also been found that when the compounds of formula (I) are reacted with phosphomonoester monoanions, the rate of reaction is at least an order of magnitude slower, i.e., the compounds of formula (I) are selective for the phosphodiester bond. This is particularly surprising because the rate of hydrolysis of both the phosphate monoester and diester is expected to be accelerated in the presence of metal complexes, with the monoester being hydrolyzed more rapidly than the diester, or if the rate of metal-catalyzed phosphodiester hydrolysis does exceed the rate for monoester hydrolysis, the difference is only a few fold.

It is further unexpected that the compounds of formula (I) hydrolyze both DNA and RNA because prior reports indicate that other copper(II) complexes which hydrolyze RNA do not hydrolyze DNA and that any cleavage of DNA by copper complexes occurs oxidatively. Differential action with respect to DNA and RNA has been predicted because RNA is more susceptible to hydrolysis than DNA, due to the presence of the 2'-OH. Thus, the compounds of formula (I) can be regarded as particularly advantageous and well-suited for catalytic hydrolytic cleavage of nucleic acids.

Surprisingly, the unusual geometry of the complexes of formula (I) favors hydrolytic cleavage of nucleic acids. The five coordinate geometry about the copper(II) is not seen in other metal complexes which tend to have octahedral or tetrahedral symmetries. Copper(II), in contrast, tends to have a square pyramidal geometry. The small chelate ring of $L^1$, particularly triazacyclononane, favors the Cu(II) oxidation state, because the ligand cannot achieve the tetrahedral coordination geometry preferred by Cu(I). This effect has been observed in Cu([9]ane$N_3$)$Cl_2$, which is irreversibly reduced in aqueous solution at 100 mV versus SCE. The low potential and the irreversibility of the reduction process indicate that the ligand destabilizes the Cu(I) oxidation state. Many metal-based DNA cleavage agents rely on activation of, for example, dioxygen or hydrogen peroxide by a reduced metal ion, and this mechanism is not possible for Cu([9]ane$N_3$)$Cl_2$.

Catalytic hydrolysis has been confirmed by studies of hydrolysis of the activated substrate bis(p-nitrophenyl) phosphate (BNPP) by the compounds of formula (I) to produce (p-nitrophenyl phosphate (NPP) and p-nitrophenolate (NP), at pH 7.2 in aqueous solution. Under the above-recited conditions, rate enhancement of more than $10_3$ over the uncatalyzed reaction is observed, and greater than stoichiometric yields of products are formed. Hydrolysis by Cu([9]ane$N_3$)$Cl_2$ is selective for the phosphodiester bond. Cleavage of the phosphomonoester, NPP, is significantly slower and is not promoted by Cu([9]ane$N_3$)$Cl_2$. FIG. 1 is a plot of initial reaction rate of the hydrolysis of the BNPP by Cu([9]ane$N_3$)$Cl_2$ versus concentration of Cu([9]ane$N_3$)$Cl_2$. The reaction is half-order with respect to Cu([9]ane$N_3$)$Cl_2$, consistent with a mechanism of catalysis by a monomeric copper complex that is in equilibrium with an inactive dimer. A value for the equilibrium constant for the conversion of monomer to dimer of 1220 $M^{-1}$ has been calculated, indicating that the majority of the copper nuclease in solution is in the inactive dimeric form. The first-order rate constant for the monomer catalyzed reaction ($k_{obs}$) of $8.86 \times 10^{-7}$ $s^{-1}$ is comparable to the rate constant for catalysis by $Cu(bpy)^{2+}$ (bpy=2,2'-bipyridyl), the only other confirmed catalyst for hydrolysis of BNPP. This represents a rate enhancement of more than $10_3$ over the spontaneous rate of BNPP hydrolysis at comparable conditions.

Figure 2:
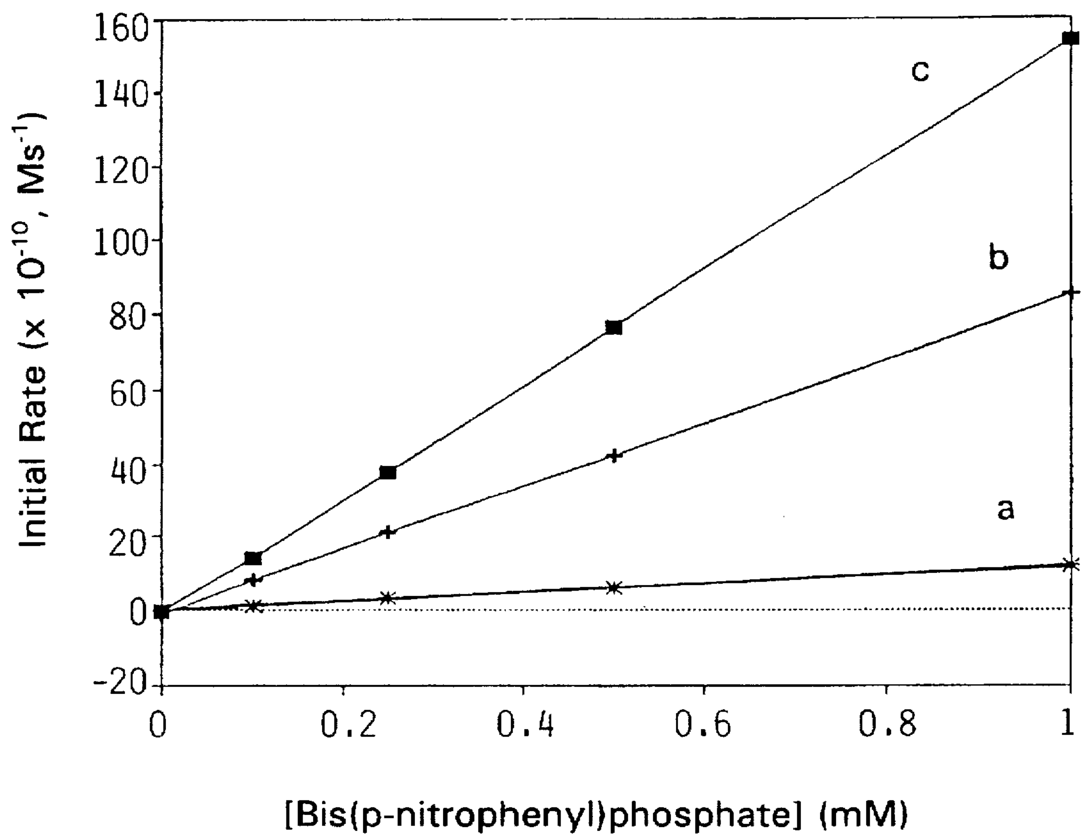
FIG. 2 is a graph of initial reaction rate (in units of $\times 10^{-10} M\ s^{-}$) v. concentration of substrate at various concentrations of the complex in accordance with the present invention.

The hydrolysis of BNPP by Cu([9]ane$N_3$)$Cl_2$ is first order in substrate, as shown in FIG. 2. Saturation is not observed even at the lowest catalyst concentration and the maximum concentration of BNPP obtainable, indicating that the substrate has a low affinity for the catalyst.

Figure 3:
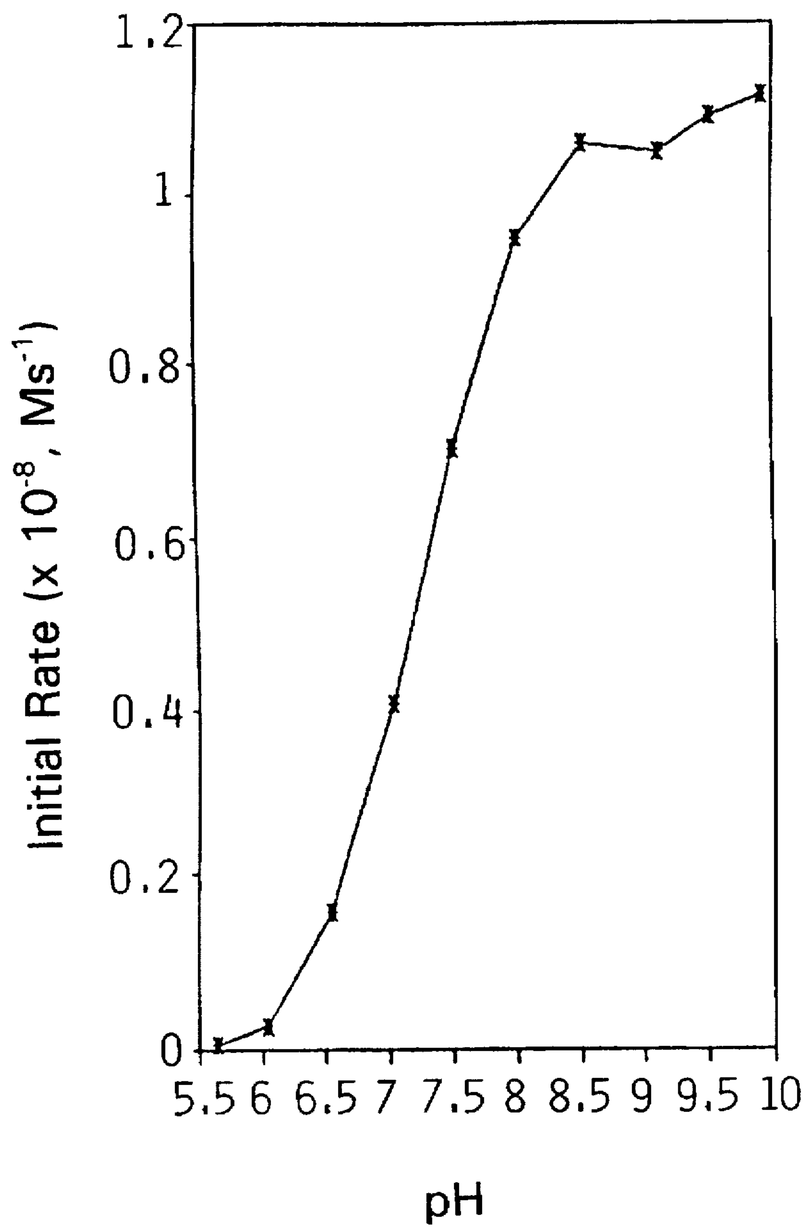
FIG. 3 is a graph of the effect of pH on hydrolysis initial reaction rate (in units of ($\times 10^{-8} M\ s^{-1}$)) by the complex in accordance with the present invention.

The effects of pH, ionic strength, and temperature on the hydrolysis of BNPP by Cu([9]ane$N_3$)$Cl_2$ have been determined. The pH dependence of the rate is shown in FIG. 3. FIG. 3 is a plot of initial reaction rate of the hydrolysis of BNPP by Cu([9]ane$N_3$)$Cl_2$ versus the pH. The reaction rate varies with 1/[H+], a result that suggests that the catalytic species is deprotonated. The $pK_a$ of the catalytic species is 7.3, as determined by a fit of the data. This $pK_a$ is the same as that which is obtained in the titration of aqueous Cu([9]ane$N_3$)$Cl_2$, and is consistent with the published $pK_a$ for the complex. These observations are consistent with the deprotonation of a water molecule bound to Cu(II), which would generate the nucleophile for attack on the phosphorus center.

The rate of hydrolysis of BNPP is inversely proportional to the ionic strength, decreasing by 30% for a 100-fold increase in ionic strength. The negative salt effect is consistent with an electrostatic contribution to the formation of the catalyst-substrate complex, i.e., the association of an anionic phosphodiester and a cationic metal complex. The activation parameters for the hydrolysis reaction have been determined from Eyring plots of reaction rate versus temperature. The activation entropy is −18.9 cal $mol^{-1}K^{-1}$ and the activation enthalpy is 20.3 kcal $mol^{-1}$. The negative entropy of activation is consistent with a bimolecular reaction.

Figure 4:
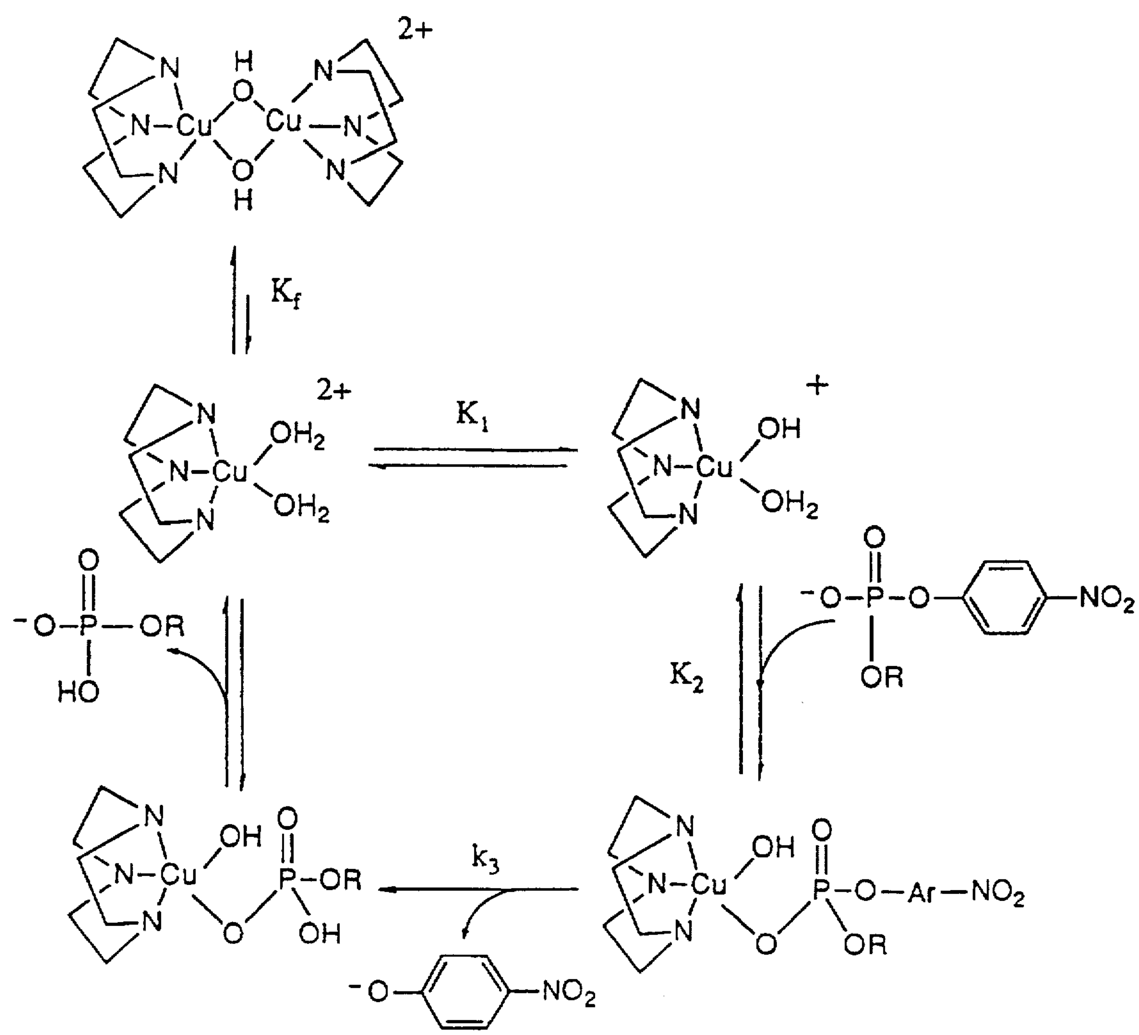
FIG. 4 is a proposed reaction mechanism for catalyzed hydrolysis of activated phosphate diesters by an illustrative composition of the present invention, $Cu[9]aneN_3Cl_2$.

A proposed mechanism for the catalytic action of the compounds of formula (I), exemplifying $Cu([9]aneN_3)Cl_2$ and BNPP, is illustrated in FIG. 4. In the proposed mechanism, the active monomer is in equilibrium with the inert dimer. The metal ion must have two open coordination sites available in order for hydrolysis to occur. One open site serves to bind the substrate and the other serves to activate a water molecule. According to this mechanism, the product, NPP, inhibits the hydrolysis of BNPP, because NPP competes with the substrate for the binding site on the metal ion. Studies have indicated that the phosphomonoester product, NPP, is an effective inhibitor of the reaction. The data do not fit simple competitive inhibition because NPP can be further hydrolyzed to produce NP.

Chelating anions will inhibit hydrolysis by binding to both open coordination sites. Pyrophosphate and oxalate anions are the most potent inhibitors yet identified; one equivalent of either oxalate anion or pyrophosphate anion completely abolishes the hydrolysis of BNPP.

The stability of the compounds of formula (I) under conditions required to cleave DNA was studied. DNA cleavage reactions required several days at elevated temperatures. Independent incubation of $Cu([9]aneN_3)Cl_2$ for two weeks in a buffered solution at physiologic pH showed no changes in either the visible spectrum or the ability of the complex to catalyze BNPP hydrolysis.

Cleavage of RNA and single-stranded DNA by $Cu([9]aneN_3)Cl_2$ has been demonstrated. The extent of cleavage of nucleic acids increases with increasing concentration of metal complex and with increasing reaction time. The concentration of Cu(II) complex is preferably in the range of 0.1 mM to 10 mM. Cleavage does not occur significantly in the absence of metal complex, although DNA requires a higher ratio of metal complex to substrate to achieve cleavage in a reasonable time period. The pH of the reaction medium is preferably near-physiological pH, i.e., pH =7.0 to 8.5, and maintained by a noncoordinating buffer. For RNA, the reaction is preferably carried out at about pH 7.2, because at pH above 7.5, the RNA is spontaneously degraded. The temperature of the reaction ranges from about 25° C. to about 55° C. The preferred reaction temperature is 37° C. for RNA and 50° C. for DNA. At higher temperatures, RNA spontaneously degrades. Significant cleavage is seen after about 6 hours for RNA and about 12 hours for single-stranded DNA.

Specifically, RNA was incubated with the complex of formula I under reaction conditions described hereinafter to produce products which appear to be consistent with hydrolytic cleavage. Degradation of double-stranded RNA occurred under the same conditions except that the incubation time was at least 12 hours.

Cleavage of the oligomer $p(T)_{20}$ (T=thymidine) by $Cu([9]aneN_3)Cl_2$, has been carried out and the reaction products have been analyzed directly by mass spectrometry. The product masses all correspond to species having an equal number of bases, sugar rings, and phosphates ($T_nS_nP_n$). This result is consistent with hydrolytic cleavage occurring between the 5' phosphate and 3' hydroxyl of the sugar ring. If the reaction proceeded via an oxidative mechanism that resulted in the loss of a base and sugar unit, then mass spectrometric analysis would have shown doublet peaks that varied by the mass of a phosphate unit (i.e., $T_nS_nP_n$ and $T_nS_nP_{n-1}$ ). Surprisingly, no cleavage products smaller than $p(T)_3$ or larger than $p(T)_{17}$ were observed.

Cleavage of the oligomer $(T)_{20}$ (i.e. there is no 5' phosphate on the end of the oligomer) has also been carried out. Mass spectrometric analysis yields product peaks that are doublets. One set of peaks corresponds to products that have an equal number of bases, sugar rings, and phosphates ($T_nS_nP_n$), while the second set of peaks corresponds to products that have one less phosphate unit $T_nS_nP_{n-1}$). These results are consistent with the results above and suggest hydrolysis between the 5' phosphate and 3' hydroxyl of the sugar ring.

Time- and concentration-dependent cleavage of single-stranded plasmid M13mp18 DNA has been demonstrated, i.e., the DNA cleavage is due to the presence of the metal complex in accordance with the present invention. The cleavage was insensitive to the presence of catalase, superoxide dimutase, methanol (as a radical trap), or to the exclusion of air, suggesting that cleavage was occurring via a nonoxidative pathway. A DNA hairpin, analogous to the RNA hairpin described herein, showed no cleavage in the double-stranded region even after one week at 50° C., although the single-stranded region was cleaved. This result indicates that single-stranded DNA is a substrate for cleavage by $Cu([9]aneN_3)Cl_2$.

Figure 5A:
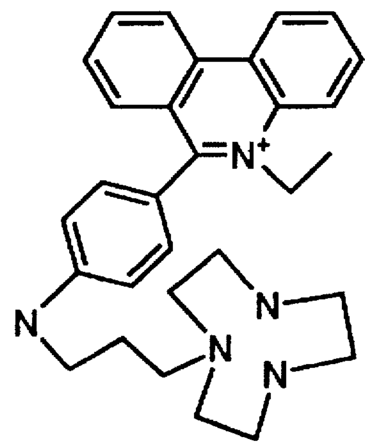
FIG. 5A is a representation of an intercalator moiety.
Figure 5A:
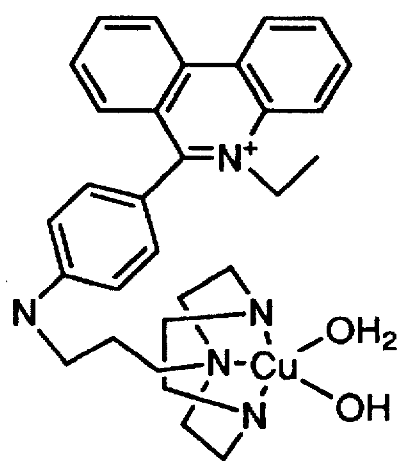

For double-stranded DNA, the method of the present invention provides an embodiment of the complex of formula (I) utilizing the ligand of formula (II) wherein Y=N—$R^3$ where $R^3$=I, an intercalator molecule. The intercalator molecule I is a recognition agent that binds to DNA, i.e., a DNA binding agent, and provides the appropriate steric conditions for the metal portion of the complex to effect cleavage. Two different strategies for the intercalators with a triazacycloalkane of the present invention are used. The two approaches differ in the site of attachment of the triazacycloalkane to the intercalator as shown in FIGS. 5A and 5A' and 5B and 5B'. Preferred among the intercalating molecules are the phenanthridines, especially ethidium and methidium.

From model building studies of the target molecules, it expected that modification of ethidium at an exocyclic amine to attach the copper triazacycloalkane will direct the metal toward the phosphodiester backbone of DNA. Phenanthridine derivatives with large modifications on both exocyclic amines have been shown to bind weakly to DNA.

Figure 6:
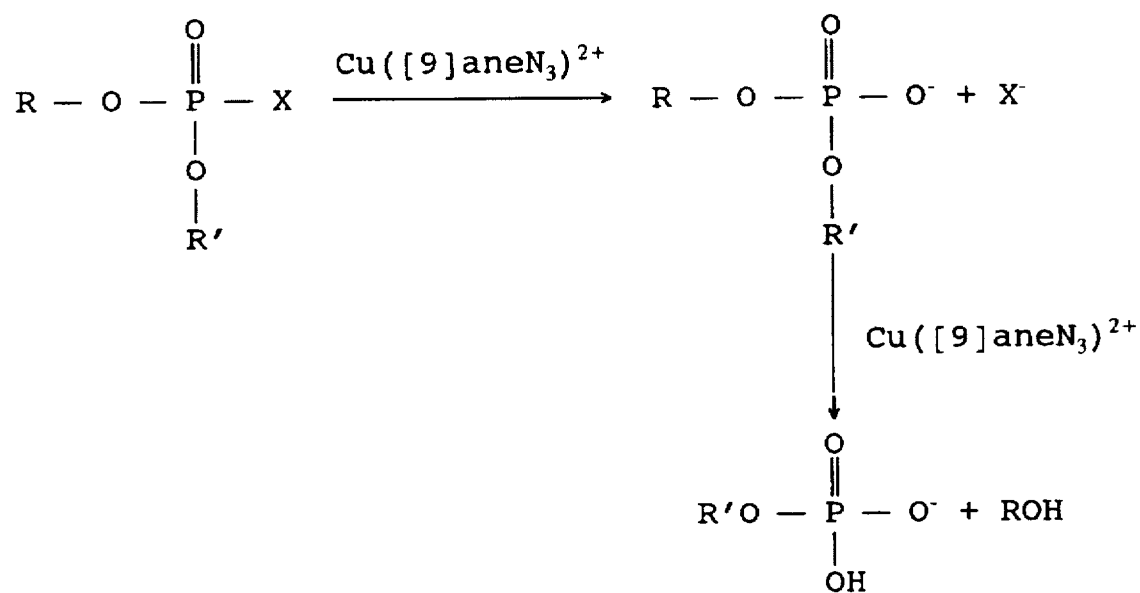
FIG. 6 is an example of hydrolysis of a general formula anticholinesterase having an oxygen-phosphorus linkage by the catalyst in accordance with the present invention.

It is also expected that the compounds of formula I are advantageously suitable for cleavage of other agents having phosphodiester linkages or derivatives thereof, e.g., anticholinesterases such as insecticides having oxygen-phosphorus linkage. To effect cleavage of such insecticides, the concentration of Cu(II) complex in accordance with the present invention is suitably in the range of 0.1 mM to 10 mM, preferably 1 mM. The concentration of the organophosphate agent is at least 0.1 mM. It is noted that the concentration of the phosphate diester is greater than the concentration of the Cu(II) complex for effective catalysis. The reaction is carried out in aqueous solution in the presence of a noncoordinating buffer, in the pH range 7.0 to 10.0. It is also noted that an extremely high ionic strength will slow the reaction. The temperature of the reaction is 50° C. or higher. It is useful to note that higher temperatures will increase the reaction rate without decomposing the Cu(II) complex of the present invention. The minimum reaction time is about 90 minutes. A proposed mechanism for decomposition of an anticholinesterase of general formula by compounds of formula (I) is illustrated in FIG. 6 where the R and R' groups are hydrocarbon groups and X is a halogen.

The compounds of formula (I) are prepared by appropriate modification of a method described by Schwindinger et al., *Inorg. Chem.*, 19 (1980) 1379–1381. The ligands $L^1$ can be prepared by appropriate modification of a method described by Smith et al., *J. Am. Chem. Soc.*, 100 (1978) 3539–44.

The present invention is further explained by the following examples which should not be construed by way of limiting the scope of the present invention. The biological buffers HEPES (N-(2-hydroxyethyl)piperazine-N'-ethanesulfonic acid), MES(2-[N-morpholino] ethanesulfonic acid potassium salt), EPPS (N-[2-hydroxyethyl] piperazine-N'-[3-propanesulfonic acid]), and CHES (2-[N-cyclohexylamino]ethanesulfonic acid) were purchased from Sigma Chemical Co. All chemicals were used without further purification. All aqueous solutions were prepared with water purified by passage through a Millipore™ Filtration System available from Millipore Corp. of Milford, Mass., U.S.A.

All pH measurements were made on an Orion research digital ion analyzer model 611, equipped with a Ross semi-micro temperature compensation electrode. Kinetic measurements were made with the use of a Hitachi U-3210 UV-Vis spectrophotometer equipped with a thermostated cell compartment. A Waters M6OOO HPLC with a Rheodyne injector and a model 440 UV detector was used for HPLC measurements. Proton nuclear magnetic resonance ($^1H$ NMR) spectra were recorded on a Bruker WP 270 in $CDCl_3$ (d-chloroform) with TMS (trimethyl silane) (Cambridge Isotope Labs, Woburn, Mass., U.S.A., or Aldrich Chemical, Milwaukee, Wis., U.S.A.), as an internal standard. NMR was only used for characterization of the organic materials. Elemental analysis was performed by Galbraith Laboratories of Knoxville, Tenn.

EXAMPLE 1

Preparation of $Cu([9]aneN_3)Cl_2$

The ligand 1,4,7-triazacyclononane ($[9]aneN_3$) was prepared by a known method (see, Koyama et al., *Bull. Chem. Soc. Jap.*, 45 (1972) 481–484; Richman et al., *J. Am. Chem. Soc.*, 96 (1974) 2268–2270; Searle et al., Aust. J. Chem., 37 (1984) 959–970), and isolated as the trihydrochloride salt. The catalyst $Cu([9]aneN_3)Cl_2$ was prepared by the method of Schwindinger et. al, (*Inorg. Chem.* 19 (1980) 1379–1381), and then purified as follows. A mixture of sodium chloride and blue plates of $Cu([9]aneN_3)Cl_2$ was dissolved in a minimum volume of hot water. The sodium chloride was selectively precipitated by the drop-wise addition of ethanol until a faint turbidity persisted in the mixture. The mixture was chilled to −20° C., the sodium chloride removed by filtration, and the catalyst recovered by evaporation over steam. The purified blue powder was recrystallized from water to yield blue plates of product. The single crystal x-ray diffraction structure was consistent with that previously reported. (Yield 70%.) Analysis: Calc'd for $C_6H_{15}N_3CuCl_2$: C, 27.33; H, 5.73; N, 15.94; Cl, 26.89. Found: C, 27.17; H, 5.96; N, 15.79; Cl, 27.25.

Other catalytic complexes with variations of the ligand were also prepared by appropriate modifications to the hereinbefore cited methods.

EXAMPLE 2

Preparation of Ligands$[12]aneN_3$, $[10]aneN_3$, and $[11]aneN_3$ 1,5,9-tritosyl-1,5,9-triazacyclododecane was prepared in the same fashion as 1,4,7-tritosyl-1,4,7-triazacyclononane (see, Koyama et al., *Bull. Chem. Soc. Jap.*, 45 (1972) 481–484; Richman et al., *J. Am. Chem. Soc.*, 96 (1974) 2268–2270; Searle et al., *Aust. J. Chem.*, 37 (1984) 959–970), using the appropriate ligand precursors. For example, the appropriate ligand precursors for the $[12]aneN_3$ were propylene glycol and dipropylenetriamine. Deprotection of the nitrogens to form $[12]aneN_3$ was accomplished by refluxing in 37% concentrated acetic acid/63% concentrated HBr for 48 hours according to the procedure of Koyama and Yoshimo (*Bull. of Chem. Soc. of Japan,* 45 (1972) 481). The volume was reduced to 1/10 original volume and the trihydrobromide salt isolated in 20% yield by precipitation with ether.

Synthesis of the ligands $[10]aneN_3$ and $[11]aneN_3$ was achieved in an identical manner. The appropriate ligand precursors for $[10]aneN_3$ were propylene glycol and diethylenetriamine. The appropriate ligand precursors for $[11]aneN_3$ were ethylene glycol and dipropylenetriamine.

EXAMPLE 3

Preparation of Ligand-$[9]aneN_2O$ 4,7-ditosyl-1-oxa-4,7-diazacyclononane was synthesized according to the procedure of Raβhofer et al. (*Liebigs Ann. Chem.*, 916 (1976) 923). Deprotection of the nitrogens and formation of the dihydrobromide salt of $[9]aneN_2O$ was accomplished as described by V. J. Thöm, M. S. Shaikjee, and R. D. Hancock (*Inorg. Chem.*, 25 (1986) 2992).

EXAMPLE 4

Preparation of Ligand-$(CH_3)_3[9]aneN_3$ and Cu(II)-$(CH_3)_3[9]aneN_3$ complex The ligand 1,4,7-trimethyl-1,4,7-triazacyclononane ($(CH_3)_3[9]aneN_3$) was synthesized according to the procedure of E. K. Barfield and F. Wagner *Inorg. Chem.*, 12 (1973) 2435). The ligand was stored as the trihydrochloride salt, $[(CH_3)_3[9]aneN_3]$.3HCl, which was generated by dissolving $(CH_3)_3[9]aneN_3$ in absolute ethanol, cooling in an ice-acetone bath, adding concentrated HCl dropwise until precipitate stops forming and then collecting the product by filtration.

The metal complex $[Cu_2((CH_3)_3[9]aneN_3)_2(\mu\text{-}Cl_3]Cl$ was synthesized by modifications to the procedures of Chaudhuri (*J. Chem. Soc. Dalton Trans.*, (1990) 1597) and Wieghardt (*Angew. Chem. Int. Ed. Entl.*, 24 (1985) 57). The free base of the ligand was prepared by dissolving 51 mg of $[(CH_3)_3[9]aneN_3]$.3HCl and 3 equivalents of NaOH in 5 ml of methanol. This solution was added to 4 ml of a methanolic solution of $CuCl_2.2H_2O$ resulting in a green mixture. Sodium chloride was precipitated by reducing the volume to approximately 3 ml and cooling to −20° C. The solution was filtered and the methanol evaporated to yield yellow crystals of $[Cu_2((CH_3)_3[9]aneN_3)_2(\mu\text{-}Cl)_3]Cl$. Removal of the solvent by drying in air or pumping under vacuum yields green crystals in 60% yield.

EXAMPLE 5

Preparation of $Cu([10]aneN_3)Br_2$

The metal complex $Cu([10]aneN_3)Br_2$ was synthesized by dissolving 50 mg of $[10]aneN_3$.3HBr (synthesized using appropriate modification to the method of Example 2) and 1 equivalent $CuBr_2$ in 1 ml $H_2O$ and slowly adding 2.95 equivalents of aqueous NaOH (0.2 ml) to give a blue solution. The volume was reduced by half over a steam bath and then doubled by addition of ethanol to yield a green solution. The solution was stored at 4° C. for 24 hours allowing green crystals to form. The crystals were collected by filtration and recrystallized by dissolving in a minimum volume of water, reducing the volume, and addition of ethanol as described above.

EXAMPLE 6

Preparation of Cu([11]ane$N_3$)$Br_2$

The metal complex Cu([11]ane$N_3$)$Br_2$ was synthesized by dissolving 50 mg of [11]ane$N_3$.3HBr (synthesized using appropriate modification to the method of Example 2) in 1 ml $CH_3CH$ and adding 2.95 equivalents of NaOH (0.2 ml) dissolved in methanol resulting in a cloudy solution. Methanol was slowly added to the cloudy solution until it turned clear. This solution was then slowly added to 1 equivalent of methanolic $CuBr_2$ (1 ml). After reducing the volume to approximately ¼ the original volume via a steam bath, the solution was stored at 4° C. for 72 hours. The resulting green precipitate was collected by filtration.

EXAMPLE 7

Preparation of Cu([12]ane$N_3$)$Br_2$

The metal complex Cu[12]ane$N_3$$Br_2$ was synthesized by dissolving 50 mg of [12]ane$N_3$.3HBr (synthesized using appropriate modification to the method of Example 2) and 2.95 equivalents of NaOH in 0.2 ml of $H_2O$ followed by the addition of 1 ml of ethanol. This solution was slowly combined with 1 equivalent of ethanolic $CuBr_2$ (1 ml) resulting in a cloudy green mixture. The mixture was stirred and slightly heated until the turbidity disappeared. The volume was reduced to 1 ml over a steam bath and then cooled to 4° C. for 1 hour. The resulting green precipitate was collected by filtration and washed in cold ethanol.

EXAMPLE 8

Demonstration of catalysis

Various concentrations (0.1 mM to 1 mM) of Cu([9]ane$N_3$)$Cl_2$ were reacted with 5 mM BNPP (bis(p-nitrophenyl) phosphate) at a pH of 7.24, controlled by 0.100M HEPES buffer. The ionic strength was maintained at 0.100M with $NaClO_4$. The total reaction time was 10 days at 51° C. stabilized by a sand bath. The reaction was carried in sealed glass cells. The reaction was followed by monitoring an increase in absorbance at 400 nm indicative of production of NP (p-nitrophenolate). The concentration of NP was determined by direct difference relative to a reference sample (identical in all respects to reaction mixture except lacking the Cu([9]ane$N_3$)$Cl_2$). The concentration of NP released was calculated from the extinction coefficient at 400 nm, 18,700 L $mol^{-1}cm^{-1}$, and corrected for pH from temperature data from Martell et al., (*Critical Stability Constants*, Plenum Press, New York, (1977) vol. 3, p. 183). The percent conversion, i.e., [NP]/[BNPP], was calculated assuming one NP produced per BNPP. The number of turnovers was calculated as $NP_{evolved}$ per metal complex.

TABLE 1

| [Cu([9]ane$N_3$)$Cl_2$] | $k_{obs}(s^{-1})$ | % Conversion | Turnovers |
|---|---|---|---|
| 1 mM | $1.33 \times 10^{-6}$ | 63.5 | 3.2 |
| 0.5 mM | $9.25 \times 10^{-7}$ | 50.5 | 5.0 |
| 0.2 mM | $4.67 \times 10^{-7}$ | 29.9 | 7.5 |
| 0.1 mM | $2.17 \times 10^{-7}$ | 20.0 | 10.2 |

Analysis of products of reaction was carried out by reverse phase HPLC on a Alltech Econosphere C-18 column, eluted with 50% methanol/50% 50 mM phosphate buffer, pH 7. Analysis showed only two peaks NPP (p-nitrophenyl phosphate) and NP, eluting at 1.4 and 3.5 min., respectively, and unreacted substrate at 4.3 min. The identity of the products was confirmed by co-injection of authentic standards. Both products were detectable at short reaction times, and the intensities of the two peaks grew at approximately the same rate over the entire reaction period.

EXAMPLE 9

Studies of change in reaction rate with increasing ligand size

Studies were conducted to determine the effect of size of the ligand macrocycle on the rate of BNPP hydrolysis. Copper(II) complexes of the 9, 10 and 11 member rings of the triazacycloalkanes were prepared as nitrates following the methods described in Examples 1, 5 and 6, with the copper(II) starting material as $Cu(NO_3)_2$. Each complex (1 mM) was incubated with 0.1 mM BNPP in 0.1M HEPES at T=50° C. and a pH of 7.24 for 60 minutes with μ=60 mM. The initial rate of reaction as described in Example 8 was measured and the results are shown in Table 2 below where "Δv" is the change in rate.

TABLE 2

Comparative Reactivities for Cu([n]ane$N_3$) $(NO_3)_2$, n = 9, 10 or 11.

| Complex | Initial Rate | Δv |
|---|---|---|
| Cu([9]ane$N_3$) $(NO_3)_2$ | $3.6 \times 10^{-10}$ M $S^{-1}$ | 1 |
| Cu([10]ane$N_3$) $(NO_3)_2$ | $7.2 \times 10^{-10}$ M $S^{-1}$ | 2 |
| Cu([11]ane$N_3$) $(NO_3)_2$ | $1.5 \times 10^{-9}$ M $S^{-1}$ | 4 |

As the results of Table 2 illustrate, the [10]ane$N_3$ complex hydrolyzed BNPP twice as fast as the [9]ane$N_3$ complex, and the [11]ane$N_3$ complex hydrolyzed BNPP twice as fast as the [10]ane$N_3$ complex. The [12]ane$N_3$ complex is expected to hydrolyze BNPP eight times faster than the [9]ane$N_3$ complex.

When 0.25 mM $Cu_2[(CH_3)_3[9]aneN_3)_2(\mu\text{-}Cl\ )_3]Cl$ was incubated with 0.5 mM BNPP under identical conditions to those used above, the initial rate of hydrolysis of BNPP was $7.6\times10^{-9}$ $Ms^{-1}$. Assuming that the order of the reaction with respect to metal and substrate is the same as for the previous reactions, and extrapolating to the same metal and substrate concentrations used in the previous experiments, the initial rate of BNPP hydrolysis by the copper(II) trimethyl triazacyclonane complex is $3.0\times10^{-9}$ $Ms^{-1}$, which is 8.5 times faster than the metal complex Cu([9]ane$N_3$) $(NO_3)_2$.

EXAMPLE 10

Cleavage of RNA

The oligonucleotide 5'-UCCCCCUC UUCGGAGGGGGA-3' (SEQ.ID NO.1) was 5'-end labelled with radioactive $^{32}P$ and allowed to anneal to itself to form a hairpin loop (loop region underlined). The oligonucleotide was synthesized on an Applied Biosystems 392 DNA/RNA Synthesizer available from Applied Biosystems of Foster City, Calif., U.S.A., using the procedure outlined in User Bulletin #69 pp. 1–15 (October 1992). The labeling of the 5' end and annealing was carried out according to the general methods described in *Molecular Cloning, A Laboratory Manual*, 2nd ed., J. Sambrook, E. F. Fritsch, and T. Maniatis, Cold Spring Harbor, Cold Spring Harbor Press (1989).

Figure 7:
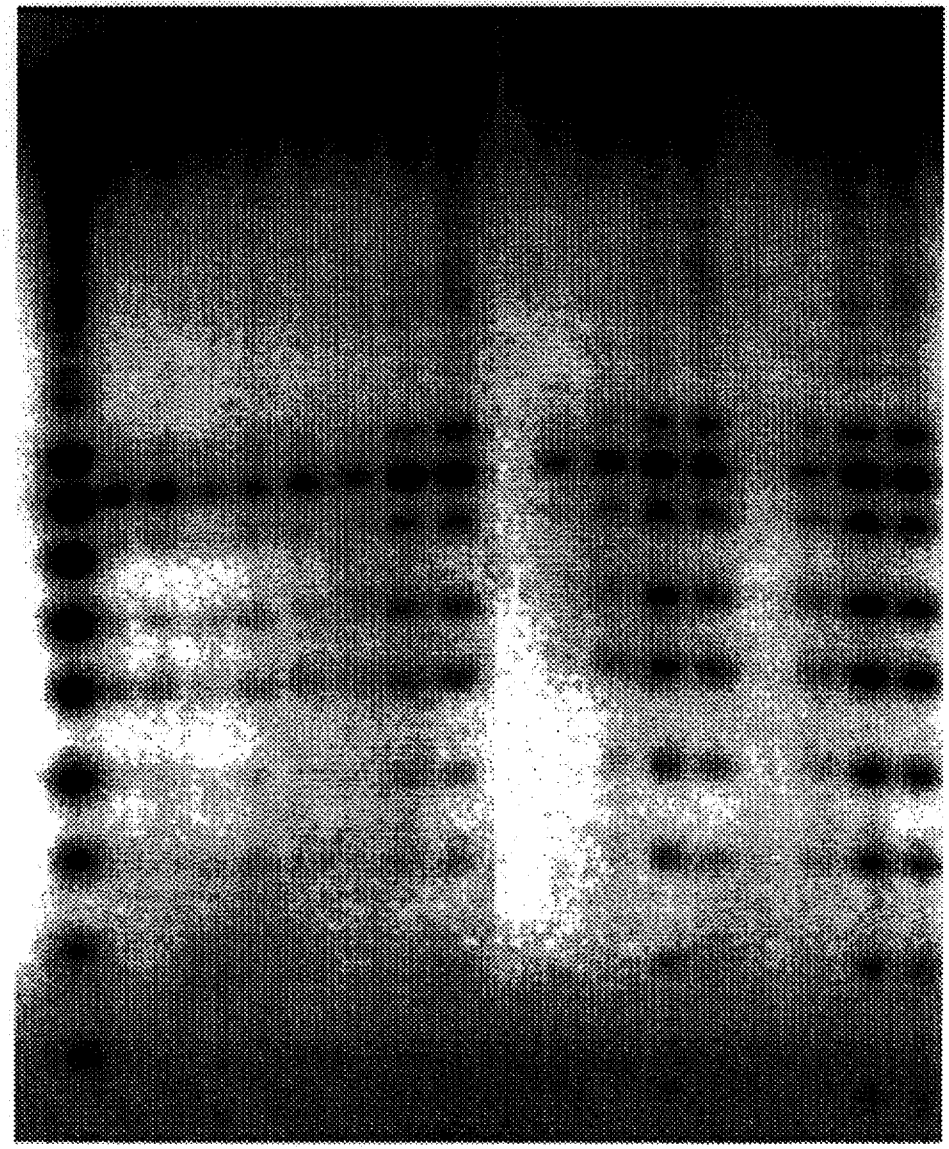
FIG. 7 is an autoradiograph of RNA cleavage products using the composition in accordance with the present invention.

20 pmol of the $^{32}P$-RNA in 20 μl (1 μM) was then incubated at 37° C. in 50 mM HEPES, pH 7.2, for 6, 12, 24, or 48 hours in the presence of varying concentrations of Cu([9]ane$N_3$)$Cl_2$ (0.1 mM to 10 mM). Aliquots of the reactions were then run on a 20% polyacrylamide denaturing gel, and the radiolabeled cleavage products visualized by autoradiography, i.e., the exposure of x-ray film to the separated products and development of the x-ray film according to standard film processing techniques. The results are indicated in Table 3 below and are shown in FIG. 7.

TABLE 3

| [Cu([9]ane$N_3$)$Cl_2$] | Incubation Time 6 hrs. | 12 hrs. | 24 hrs. | 48 hrs. |
|---|---|---|---|---|
| 0 (control) | 0 | 0 | 0 | 0 |
| 0.1 mM | 0 | + | + | + |
| 1.0 mM | 0 | + | + | + |
| 10.0 mM | + | + | + | + |

0 = no cleavage of RNA
+ = cleavage of RNA

The lanes of the autoradiograph are as follows:

Lane 1: RNA base hydrolysis ladder.

Lanes 2,6,10: Control, no metal complex.

Lanes 3,7,11,15: 0.1 mM Cu([9]ane$N_3$)$Cl_2$.

Lanes 4,8,12,16: 1.0 mM Cu([9]ane$N_3$)$Cl_2$.

Lanes 5,9,13,17: 10 mM Cu([9]ane$N_3$)$Cl_2$.

Lanes 2–5: 6 hours incubation.

Lanes 6–9: 12 hours incubation.

Lanes 10–13: 24 hours incubation.

Lanes 14–16: 48 hours incubation.

Comparison of lane 6 (the RNA was incubated for 12 hours in the absence of the metal complex) with lanes 8 and 9 (the RNA was incubated for the same length of time in the presence of 1.0 mM and 10 mM metal complex, respectively.) shows that the RNA cleavage is dependent on the presence of the metal complex. Identical results were seen at 24 hours and cleavage products continue to be seen at 48 hours. Significant cleavage was seen after 6 hours of incubation of the RNA at the highest metal concentration.

RNA cleavage was not inhibited by the inclusion of catalase, superoxide dismutase, or picolinic acid (as a free radical trap) in the reaction mixture, suggesting that a nonoxidative cleavage mechanism is operative. The products of the cleavage reaction co-migrate with the products of RNA base hydrolysis, indicating that the cleavage is hydrolytic. Analysis of the autoradiographic data indicates that the initial site of cleavage is in the loop region of the hairpin; however, at longer reaction times, cleavage of the double-stranded region is observed.

EXAMPLE 11

Cleavage of single-stranded $(T)_{20}$ (nonphosphorylated 5' end) using Cu([9]ane$N_3$)$Cl_2$ A single-stranded $(T)_{20}$ oligomer was synthesized on an Applied Biosystems, 392 DNA/RNA Synthesizer (Applied Biosystems, Foster City, Calif., U.S.A.) using the materials and procedure outlined in User Bulletin #69. The cleavage of this single-stranded poly-T (T=thymidine) oligomer $[(T)_{20}]$, which is 20 units long and has no phosphate at the 5' end, was conducted, by incubating 0.2 mM (1.2 g/l) of $(T)_{20}$ at pH 7.8 in 50 mM HEPES buffer at 50° C. for 6 days with 0.5 mM of Cu([9]ane$N_3$)$Cl_2$.

Figure 8:
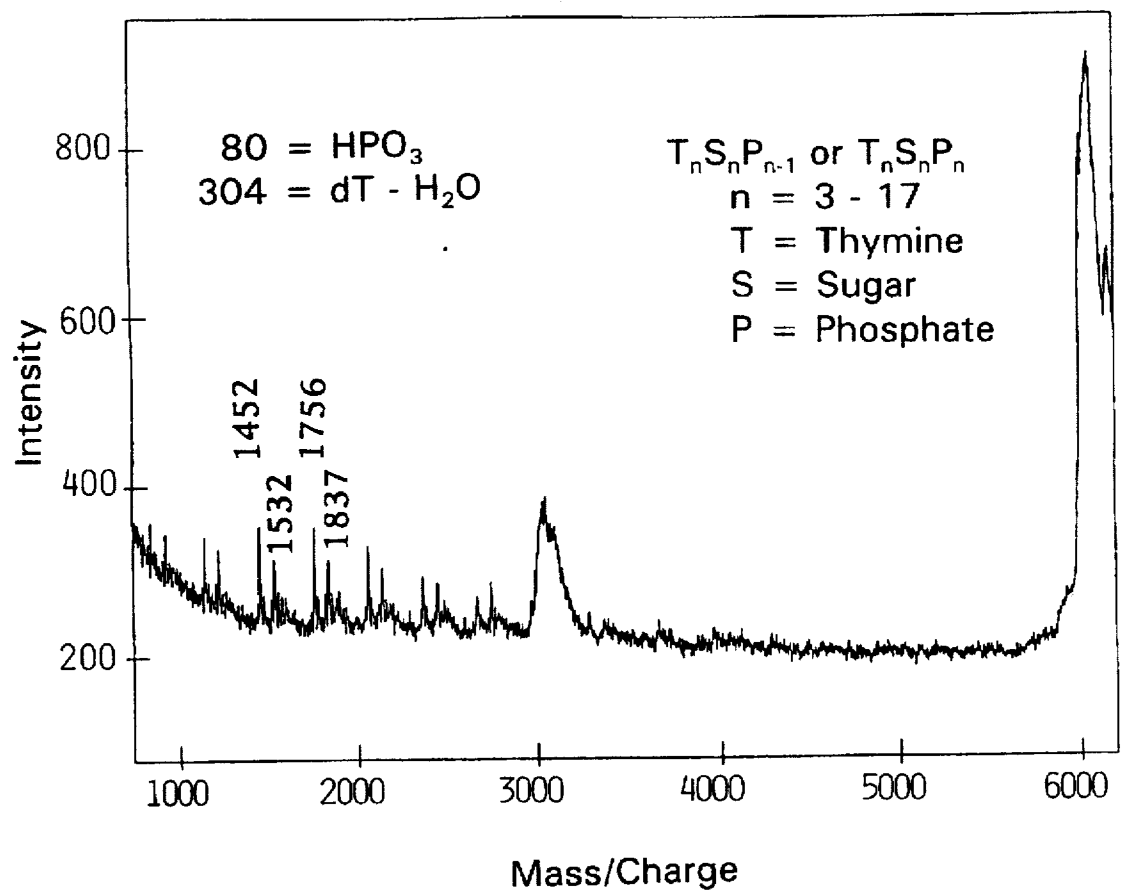
FIG. 8 is a mass spectrum of $(T)_{20}$ cleavage products using the composition in accordance with the present invention.

Mass spectrometric analysis was undertaken on the products of reaction and the spectral results are shown in FIG. 8.

The results of analysis show that cleavage of poly-T oligomer gives doublet peaks corresponding to $T_nS_nP_n$ and $T_nS_nP_{n-1}$ where T is thymine, P is phosphate, S is ribose and n is a number between 3 and 17. The results support a hydrolytic cleavage as most oxidative cleavage mechanisms involve loss of a base and sugar unit.

EXAMPLE 12

Cleavage of single-stranded $p(T)_{20}$ (phosphorylated 5' end) using Cu([9]ane$N_3$)$Cl_2$ 0.3 mM (1.8 g/l) of $P(T)_{20}$ having a phosphorylated 5' end was incubated at pH 7.2 in 2 mM HEPES buffer at 50° C. for 3 days with 0.5 mM Cu([9]ane$N_3$)$Cl_2$. The oligomer, which is a single-stranded oglionucleotide composed of 20 thymidines, was obtained from the University of Wisconsin Biotechnology Center, Madison, Wis., U.S.A. Alternatively, the oligomer can be synthesized using the Applied Biosystems 392 DNA/RNA Synthesizer as described in Example 11.

Figure 9:
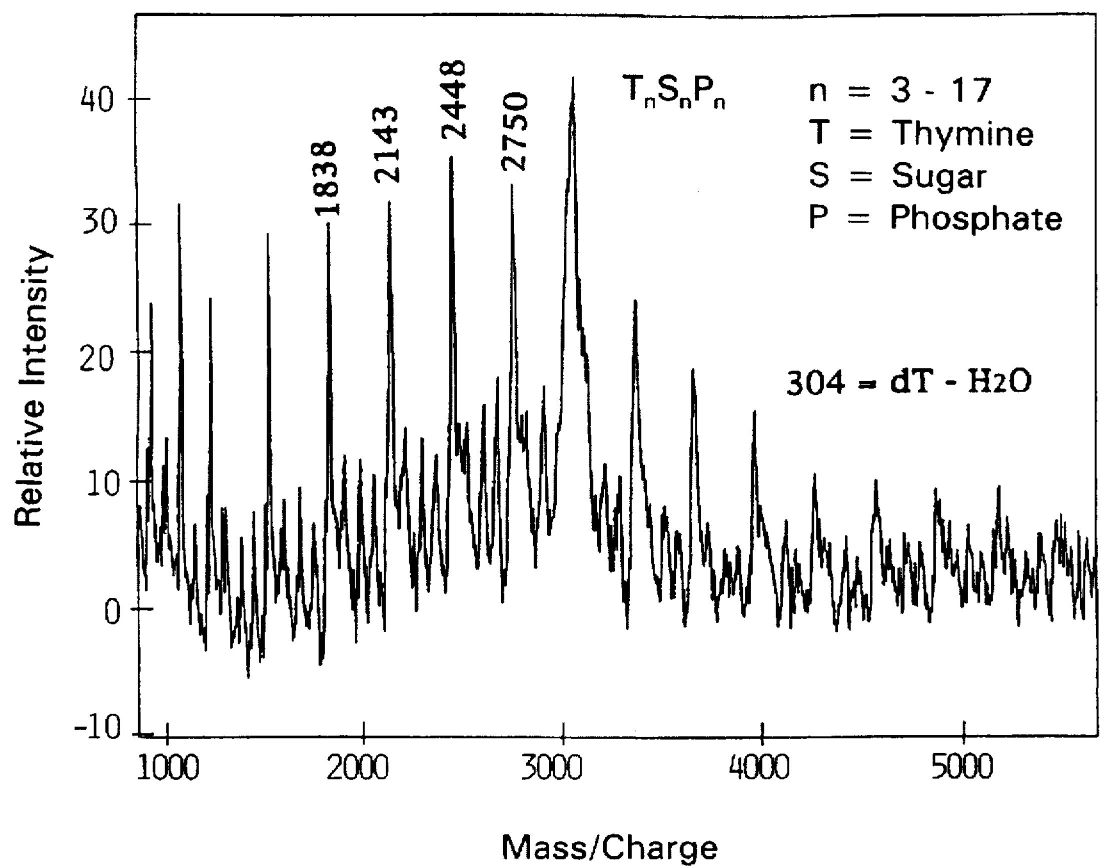
FIG. 9 is a mass spectrum of 5' $p(T)_{20}$ cleavage products using the composition in accordance with the present invention.

Mass spectrometric analysis was undertaken on the products of reaction and the spectral results are shown in FIG. 9.

The results of the analysis show that cleavage of phosphorylated 5' end poly-T oligomer gives a single family of products corresponding to $T_nS_nP_n$ where T, P, S and n are as described in Example 11. The results support that hydrolytic cleavage is preferred between the 5' phosphate and the 3' hydroxyl. If cleavage were oxidative, the T:S:P ratio would not be a 1:1:1 ratio because most oxidative cleavages involve loss of a base and sugar unit.

EXAMPLE 13

Cleavage of single-stranded DNA using Cu([9]ane$N_3$)$Cl_2$

Figure 10:
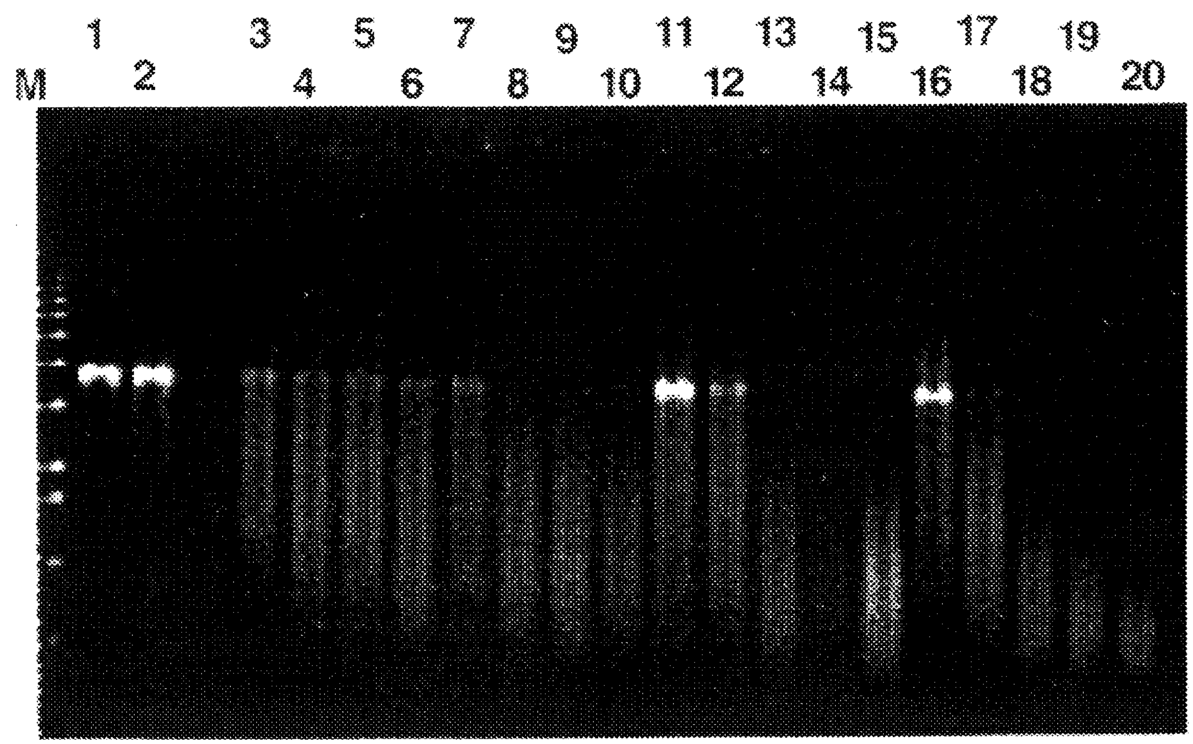
FIG. 10 is an agarose gel electrophoretic analysis of DNA cleavage products using the composition in accordance with the present invention.

Single-stranded plasmid M13mp18 DNA obtained from Pan Vera Corporation, Madison, Wis., U.S.A., (also commercially available from New England Biolabs, Inc., Beverly, Mass., U.S.A., as item #404c) was incubated at 50° C. in 50 mM HEPES, pH 7.8, for 6, 12, 24 or 48 hours with various concentrations (0.25 mM to 1.0 mM) of Cu([9]ane$N_3$)$Cl_2$. The DNA was electrophoresed on a 0.8% agarose gel, ethidium bromide stained, and photographed while ultraviolet irradiated. The results are shown in Table 4 and FIG. 10.

TABLE 4

| [Cu([9]aneN$_3$)Cl$_2$] | Incubation Time | | | |
|---|---|---|---|---|
| | 6 hrs. | 12 hrs. | 24 hrs. | 48 hrs. |
| 0 | 0 | + | 0 | 0 |
| 0.25 mM | + | + | + | + |
| 0.50 mM | + | + | + | + |
| 0.75 mM | + | + | + | + |
| 1.0 mM | + | + | + | + |

0 = no cleavage of DNA
+ = cleavage of DNA

The lanes of the electrophoretic plate were as follows:

Lane 1: Unincubated single-stranded M13mp18 DNA.

Lanes 2,6,11,16: Control (no metal complex).

Lanes (missing), 7,12,17: 0.25 mM Cu([9]aneN$_3$)Cl$_2$.

Lanes 3,8,13,18: 0.5 mM Cu([9]aneN$_3$)Cl$_2$.

Lanes 4,9,14,19: 0.75 mM Cu([9]aneN$_3$)Cl$_2$.

Lanes 5,10,15,20: 1.0 mM Cu([9]aneN$_3$)Cl$_2$.

Lanes 2–5: 6 hours incubation.

Lanes 6–10: 12 hours incubation.

Lanes 11–15: 24 hours incubation.

Lanes 16–20: 48 hours incubation.

Unincubated M13mp18 DNA was observed as a single band on the agarose gel while M13mp18 that was degraded was observed as a smear under the band: the greater the extent of cleavage, the smaller the fragments and the farther the smear is under the band. Although some degradation of the DNA occurred in the absence of the metal complex (e.g., comparing lanes 6, 11 and 16 with lane 1) at 12, 24 and 48 hours, substantial enhancement of the rate of cleavage of the DNA occurred in the presence of the metal complex, particularly at the higher concentrations. This enhancement was both time and copper complex concentration dependent. Cleavage was seen as early as 6 hours; however, the greatest extent of cleavage is seen in the DNA treated for 48 hours with 1.0 mM Cu([9]aneN$_3$)Cl$_2$ (lane 20).

EXAMPLE 14

Cleavage of double-stranded DNA

Figure 5B:
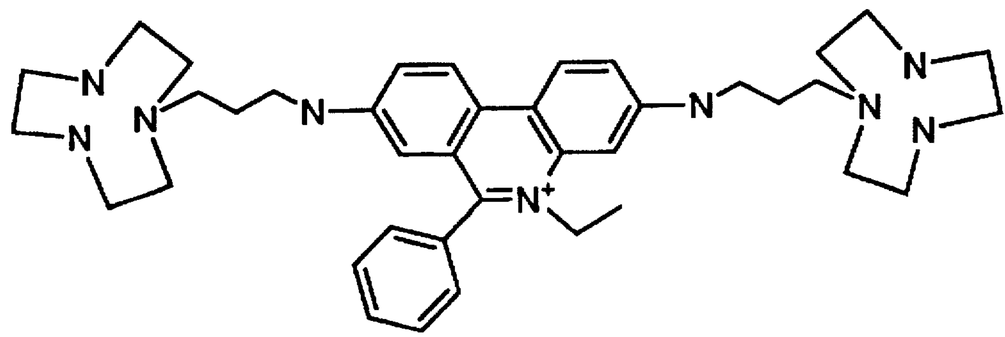
FIG. 5B is a representation of the intercalator moiety with alternate attachment sites.
Figure 5B:
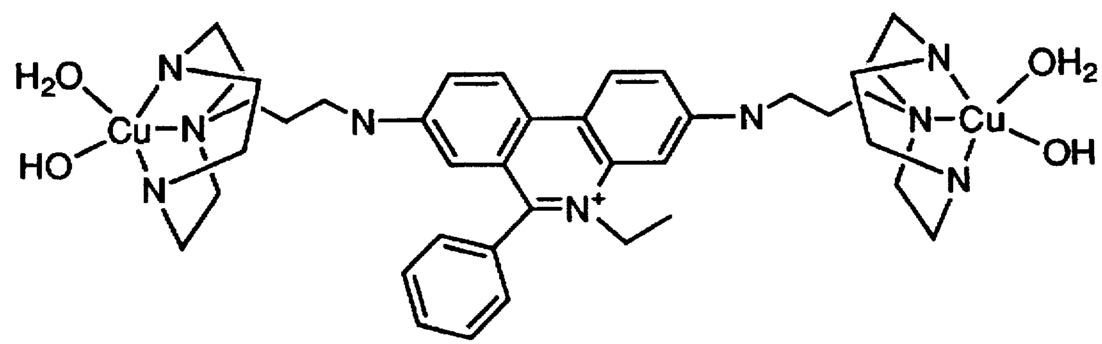

Modified phenanthridines containing appended metal chelates are synthesized to cleave double-stranded DNA. To accomplish the functionalization of methidium or ethidium, a functionalized triazacyclononane ligand is synthesized according to the following procedures. 1,4-ditosyl-1,4,7-triazacyclononane is first prepared as described by A. E. Martin et al. (*J. Org. Chem.*, 47 (1982) 412). 1-allyl-1,4,7-triazacyclononane is then prepared from the 1,4-ditosyl-1,4,7-triazacyclononane and allyl chloride by reaction in DMF (dimethylformamide) and the double bond is converted to the alcohol by hydroboration and hydrolysis according to standard protocols (see, Larock, Richard G., *Comprehensive Organic Transformations*: A Guide to Functional Group Preparations, VCH Publishers, Inc., New York, N.Y. (1989) ). Oxidation of the alcohol (see, Corey, S., *Tet. Lett.*, (1975) 2647) provides the aldehyde which is used to modify the phenanthridine on the phenyl ring by the method of Hertzberg and Dervan (R. P. Hertzberg and P. B. Dervan, *Biochem.*, 23 (1984) 3934–3945) to prepare the bifunctional intercalator-chelate shown in FIG. 5A. Alternatively, the method of Keck and Lippard (*Tet. Lett.*, 34 (1993) 1415–1416) is used to attach triazacyclononane to the exocyclic amine of methidium to make the bifunctional intercalator-chelate shown in FIG. 5B. Because Cu([9]aneN$_3$)Cl$_2$ hydrolyzes amides, the amide linkages are reduced by standard methods (Larock, *Comprehensive Organic Transformations*, supra, p. 432). The copper complexes, shown in FIGS. 5A' and 5B', of the respective intercalator-chelates are prepared by reaction of the ligand with an appropriate copper salt, such as CuBr$_2$, in water and precipitated with ethanol, as described previously. The copper complexes are characterized by standard methods of IR, NMR, ESR spectroscopy and by standard techniques of elemental analysis.

The DNA binding properties and DNA cleavage activities of the phenanthridine-Cu([9]aneN$_3$)Cl$_2$ are determined as described below. The binding affinity of the phenanthridine-Cu([9]aneN$_3$)Cl$_2$molecules to double-stranded DNA is evaluated by gel electrophoretic unwinding assays, and hyperchromicity and viscosity measurements as has been previously described (see, E. C. Long and J. K. Barton, *Acc. Chem. Res.*, 23 (1990) 273–279).

The ability of phenanthridine-Cu([9]aneN$_3$)Cl$_2$ to nick supercoiled plasmid M13mp18 DNA, obtained by a standard protocol (see, J. Sambrook, E. F. Fritsch, and T. Maniatis, *Molecular Cloning: A Laboratory Manual*, 2nd ed., Cold Spring Harbor Press, Cold Spring Harbor, N.Y. (1989)) is analyzed by agarose gel electrophoresis. The supercoiled M13mp18 DNA is incubated with phenanthridine-Cu([9]aneN$_3$)Cl$_2$, Cu([9]aneN$_3$)Cl$_2$, and phenanthridine, and the extent of conversion of supercoiled DNA to relaxed circular or linear forms is determined by agarose gel electrophoresis. All incubations are carried out in the dark to minimize nicking of the plasmid by the phenanthridine. The incubations are carried out at a temperature range of 25° C. to about 55° C., preferably at 50° C., in 50 mM HEPES, pH 7.8, for 6, 12, 24 or 48 hours with ranging concentration (0.1 mM to 1.0 mM) of the phenanthridine-Cu([9]aneN$_3$)Cl$_2$.

The ability of phenanthridine-Cu([9]aneN$_3$)Cl$_2$ to nick supercoiled plasmid DNA is compared with its ability to cleave poly(dA.dT), available from Sigma Chemical Co., St. Louis, Mo., U.S.A. End labelled 5' $^{32}$P-poly(dA.dT), is prepared by using the technique to radiolabel the 5' end with $^{32}$P as previously described in Example 10. The end labelled 5' $^{32}$P poly(dA.dT) is incubated with phenanthridine-Cu([9]aneN$_3$)Cl$_2$, Cu([9]aneN$_3$)Cl$_2$, and phenanthridine, and cleavage assayed on sequencing gels. Comparison of the band positions on the sequencing gels with those of Maxam-Gilbert sequencing lanes are made to determine whether the cleavage products have only phosphate and hydroxyl termini. The reaction mixtures are also assayed by HPLC for evidence of the release of thymine and adenine. The absence of free bases and additional bands on the sequencing gels suggests that cleavage is hydrolytic.

Experiments on unlabelled poly(dA.dT) are conducted to quantify the ratio of 3' and 5' phosphate and hydroxyl termini in the products. Aliquots of the cleavage products are phosphorylated with $^{32}$P-dideoxy-ATP by terminal transferase (3' specific) and with $^{32}$P-ATP by polynucleotide kinase (5' specific). The amount of radiolabel incorporated in the respective reaction is proportional to the number of 3' or 5' hydroxyl termini produced. The ratio of 3' and 5' phosphoryl ends is determined by difference. By treating the cleavage products with alkaline phosphatase prior to phosphorylation with either terminal transferase or polynucleotide kinase, the total of 3' and 5' hydroxyl ends is determined. From the difference between the first and second experiment, the proportion of phosphorylated ends of each type is calculated. The presence of a 1:1 ratio of phosphoryl and hydroxyl termini, each accounting for one half of the total, strongly supports hydrolytic cleavage. In addition, these experiments reveal any regioselectivity in the cleavage of DNA by phenanthridine-Cu([9]ane$N_3$)$Cl_2$.

The results show that cleavage of double-stranded DNA is achievable, when the metal complex is delivered appropriately to the double-stranded DNA molecule by phenanthridine-Cu([9]ane$N_3$)$Cl_2$.

EXAMPLE 15

Decomposition of anticholinesterases by Cu[9]ane$N_3Cl_2$

The ability of Cu([9]ane$N_3$)$Cl_2$ and other compounds in accordance with the present invention for hydrolytic decomposition of phosphate-derivative anticholinesterases such as insecticides is determined. The relatively nontoxic analogs, O-ethyl S-ethyl methylphosphonothiolate, and diethylthiophosphate, are used in these experiments as models for the hydrolytic decomposition of the phosphate-derivative anticholinesterases such as thiophosphate ester insecticides, e.g., parathion and malathion. The phosphonothiolate or thiophosphate ester (0.1 mM–10 mM) is reacted with Cu([9]ane$N_3$)$Cl_2$ (0.1 mM–1 mM) in ethanol and/or water solvent at pH 7.0–10.0, maintained with HEPES buffer, and an ionic strength of 0.1M, maintained with $NaNO_3$, at 50° C. for 90 minutes to three hours. It is noted that the concentration of the organo-phosphate is greater than the concentration of the Cu(II) complex for effective catalysis. As the pH increases, the rate of competing noncatalytic reactions increases. It is also noted that an extremely high ionic strength will slow the reaction. The temperature of the reaction is 50° C. or higher. It is useful to note that higher temperatures will increase the reaction rate without decomposing the Cu(II) complex. The minimum reaction time is about 90 minutes.

The reaction is monitored by $^{31}P$ and $^{1}H$ NMR spectroscopy, and the products identified by their characteristic NMR spectra. The rate of reaction in the presence and absence of the metal complex is determined by integration of the product NMR signals, and the rate enhancement is assessed. The order of reaction with respect to substrate and product is determined by varying the concentrations of the appropriate reagent over at least one order of magnitude. Turnover by the metal complex is demonstrated by reaction of an excess of the phosphodiester substrate with the metal complex and the production of greater than stoichiometric amounts of product. The results of these experiments show that Cu[9]ane$N_3Cl_2$is a catalyst for the hydrolysis of thiophosphate and phosphonothiolate esters and is applicable to the decomposition of insecticides with similar functionalities.

The present invention further comprehends a kit for cleaving the oxygen-phosphorus linkages of RNA or DNA with the kit comprising a cleavage incubation composition comprising a copper(II) triazacycloalkane cleaving agent in aqueous solution at a physiologically acceptable pH and ionic strength. Preferably the concentration of the cleaving agent is between 0.1 mM and 10 mM.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. A method of nonoxidatively cleaving the phosphorus-oxygen linkage of a substrate which is DNA or RNA comprising the step of cleaving the DNA or RNA phosphorus-oxygen linkages with an effective amount of the following metallo-nuclease:

$$L^1—M—L^2_b$$

wherein:

M is a pentacoordinate metal ion;

$L^1$ is tridentate facially chelating ligand which is a heterocycle having 3 heteroatoms and from 6 to 9 carbon atoms within the heterocycle; and $L^2$ is a substitutionally labile ligand disposed around M in cis coordinate positions and b is an integer having a value of 1 or 2.

2. The method of claim 1, wherein M is $Cu^{2+}$.

3. The method of claim 2, wherein $L^1$ is

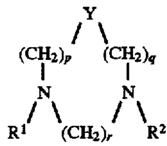

wherein:

p, q, and r are integers having the values 2 or 3;

$R^1$ and $R^2$ are each independently hydrogen or $C_1$–$C_6$ alkyl; and

Y is oxygen, sulfur or N—$R^3$ wherein $R^3$ is hydrogen, $C_1$–$C_6$ alkyl or I, wherein I is an intercalator moiety.

4. The method of claim 1, wherein $L^2$ is $X^6$ which is a catalytically acceptable anion, and wherein e is the absolute value of the charge on X and (e b)=2.

5. The method of claim 3, wherein Y is N—$R^3$; $R^1$, $R^2$ and $R^3$ are each hydrogen; and p, q and r are each equal to 2, whereby $L^1$ is represented by the formula, [9]ane$N_3$.

6. The method of claim 3, wherein Y is N—$R^3$; $R^1$, $R^2$ and $R^3$ are each hydrogen; p equals 3; and q and r are each equal to 2, whereby $L^1$ is represented by the formula, [10]ane$N_3$.

7. The method of claim 3, wherein Y is N—$R^3$; $R^1$; $R^2$ and $R^3$ are each hydrogen; p and q equal 3; and r equals 2, whereby $L^1$ is represented by the formula, [11 ]ane$N_3$.

8. The method of claim 3 wherein Y is N—$R^3$; $R^1$, $R^2$ and $R^3$ are each hydrogen; and p, q and r are each equal to 3, whereby $L^1$ is represented by the formula, [12 ]ane$N_3$.

9. The method of claim 4, wherein X is Br, Cl, $ClO_4^-$, $CF_3SO_3^-$ or $NO_3$— and said cleaving step occurs in an aqueous medium.

10. The method of claim 3, wherein I is a phenanthridine derivative which is ethidium or methidium.

11. The method of claim 1, wherein said metallo-nuclease is $Cu([9]aneN_3)Cl_2$.

12. The method of claim 3, wherein Y is oxygen.

13. The method of claim 3, wherein Y is sulfur.

14. The method of claim 3, wherein $R^1$ and $R^2$ are each a methyl group; Y is N—$R^3$ and $R^3$ is a methyl group, whereby $L^1$ is represented by the formula

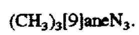

$(CH_3)_3[9]aneN_3$.

15. The method of claim 1, wherein said cleaving step occurs catalytically.

16. The method of claim 1, wherein said cleaving step occurs hydrolytically.

17. The method of claim 1, wherein said amount of said metallo-nuclease is between 0.1 mM and 10 mM.

18. The method of claim 1, wherein said substrate is RNA and said cleaving step is conducted at a pH of about 7.0 to about 7.5 and at a temperature of about 25° C. to 37° C.

19. The method of claim 1, wherein said substrate is DNA and said cleaving step is conducted at a pH of about 7.8 to 8.5 and at a temperature of about 25° C. to about 55° C.

20. The method of claim 1, wherein said cleaving step is conducted for a reaction period of between about 6 hours and 48 hours.

21. The method according to claim 3 wherein said substrate is RNA is present at a concentration of 1 μM; said amount of said metallo-nuclease complex is at least 0.1 mM; and said cleaving step is conducted at a pH of about 7.2, a temperature of about 37° C. and a reaction period of greater than 6 hours.

22. The method according to claim 10, wherein said substrate is DNA and is present at a concentration of 0.05 mg/ml; said amount of said metallo-nuclease is at least 0.1 mM; and said cleaving step is conducted at a pH is about 7.8, a temperature of about 50° C., and a reaction period of at least 6 hours.

23. A kit for cleaving the oxygen-phosphorus linkages of RNA or DNA, said kit comprising a cleavage incubation composition comprising a copper(II) triazacycloalkane cleaving agent in aqueous solution at a physiologically acceptable pH and ionic strength, wherein said copper(II) triazacycloalkane cleaving agent is represented by the formula $Cu([n]aneN_3)X_2$ wherein $[n]aneN_3$ represents a heterocyclic ring having three nitrogen atoms, X is a catalytically acceptable anion which is $Br^-$, $Cl^-$, $ClO_4^{31}$, $CF_3SO_3^-$, $NO_3^-$ or combinations thereof, and wherein n is an integer ranging from 9 to 12 which is the total number of atoms in the heterocyclic ring.

24. The kit of claim 23, wherein the concentration of said cleaving agent is between 0.1 mM and 10 mM.

25. A method of decomposing agents which are anticholinesterases having oxygen-phosphorus linkages, comprising the step of reacting the agents with an effective amount of a complex represented by the formula

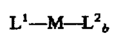

$L^1$—M—$L^2_b$ wherein:

$L^1$ is

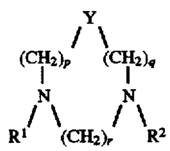

wherein:

p, q, and r are integers having the values 2 or 3;

$R^1$ and $R^2$ are each independently hydrogen or $C_1$–$C_6$ alkyl; and

Y is oxygen, sulfur or N—$R^3$ wherein $R^3$ is hydrogen, $C_1$–$C_6$ alkyl or I wherein I is a phenanthradine derivative which is ethidium or methidium;

M is $Cu^{2+}$; and $L^2$ is $X^e$ which is catalytically acceptable anion, and wherein e is the absolute value of the charge on X and e times b equals 2, wherein X is $Br^-$, $Cl^-$, $ClO_4^-$, $CF_3SO_3^-$, $NO_3$— or a combination thereof.

26. A composition comprising a synthetic nonenzymatic metallo-nuclease represented by the formula $L^1$—M—$L_{2b}$ wherein:

$L^1$ is a heterocycle having 3 heteroatoms and from 6 to 9 carbon atoms;

M is $Cu^{2+}$; and $L^2$ is $X^e$ which is a catalytically acceptable anion, and wherein e is the absolute value of the charge on X and e times b equals 2, in aqueous solution at a physiologically acceptable pH and ionic strength, said nuclease being in an amount which is capable of cleaving the phosphorus-oxygen linkage of DNA or RNA, said X being selected from the group consisting of $Br^-$, $Cl^-$, $ClO_4^-$, $CF_3SO_3^-$, $NO_3^-$ and combinations thereof.

27. The composition of claim 26, wherein $L^1$ is

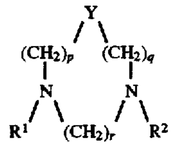

wherein:

p, q, and r are integers having the values 2 or 3;

$R^1$ and $R^2$ are each independently hydrogen or $C_1$–$C_6$ alkyl; and

Y is oxygen, sulfur or N—$R^3$ wherein $R^3$ is hydrogen, $C_1$–$C_6$ alkyl or I wherein I is an intercalator moiety.

28. The composition of claim 27, wherein I is a phenanthridine derivative which is ethidium or methidium.

29. The composition of claim 26, wherein said catalytically acceptable anion has an aqueous exchange rate constant of $k \sim 10^9 s^{-1}$ in aqueous solutions.

30. The composition of claim 26, wherein said catalytically acceptable anion is $Br^-$, $Cl^-$, $CF_3SO_3^-$, or $NO_3^-$.

* * * * *

UNITED STATES PATENT AND TRADEMARK OFFICE
CERTIFICATE OF CORRECTION

PATENT NO. : 5,739,022

DATED : April 14, 1998

INVENTOR(S) : Judith N. Burstyn, Eric L. Hegg and Kim A. Deal

It is certified that error appears in the above-identified patent and that said Letters Patent is hereby corrected as shown below:

Col 4, line 67 "phosphorous-oxygen" should read --phosphorus-oxygen--.

Col 5, line 34 "$Ms^{-})$" should read --$Ms^{-1})$--.

Col. 8, line 21 "$10_3$" should read --$10^3$--.

Col. 8, line 39 "$10_3$" should read --$10^3$--.

Col. 12, line 39 "$[(CH_3)_3[9]aneN_3].3HCl$" should read --$[(CH_3)_3[9]aneN_3]\cdot 3HCl$--.

Col. 12, lines 48-49 "$[(CH_3)_3[9]aneN_3].3HCl$" should read --$[(CH_3)_3[9]aneN_3]\cdot 3HCl$--.

Col. 12, line 51 "$CuCl_2.2H_2O$" should read --$CuCl_2\cdot 2H_2O$--.

Col. 12, line 63 "$[10]aneN_3.3HBr$" should read --$[10]aneN_3\cdot 3HBr$--.

Col. 13, line 14 "$[11]aneN_3.3HBr$" should read --$[11]aneN_3\cdot 3HBr$--.

Col. 13, line 16 "$CH_3CH$" should read --$CH_3Cl$--.

Col. 13, line 32 "$[12]aneN_3.3HBr$" should read --$[12]aneN_3\cdot 3HBr$--.

Col. 14, line 46 (TABLE 2) "$M\ S^{-1}$" should read --$M\ s^{-1}$--.

Col. 14, line 47 (TABLE 2) "$M\ S^{-1}$" should read --$M\ s^{-1}$--.

Col. 14, line 48 (TABLE 2) "$M\ S^{-1}$" should read --$M\ s^{-1}$--.

Col. 16, line 32 "$P(T)_{20}$"should read --$p(T)_{20}$--.

Col. 18, line 39 "poly(dA.dT)" should read --poly(dA·dT)--.

UNITED STATES PATENT AND TRADEMARK OFFICE

CERTIFICATE OF CORRECTION

PATENT NO. : 5,739,022 Page 2 of 2

DATED : April 14, 1998

INVENTOR(S) : Judith N. Burstyn, Eric L. Hegg and Kim A. Deal

It is certified that error appears in the above-identified patent and that said Letters Patent is hereby corrected as shown below:

Col. 18, line 40 "5' $^{32}$P-poly(dA.dT)" should read --5' $^{32}$P-poly(dA·dT)--.

Col. 18, line 43 "5' $^{32}$P-poly(dA.dT)" should read --5' $^{32}$P poly(dA·dT)--.

Col. 18, line 53 "poly(dA.dT)" should read--poly(dA·dT)--.

Col. 21, line 20 (Claim 4, 1st line) "$X^{6}$" should read --$X^{e}$--.

Col. 22, line 26 (Claim 23, 9th line) "$ClO_4^{31}$"should read --$ClO_4^-$--.

Col. 22, line 65 (Claim 26, 3rd line) "$L^1$-M-$L_{2b}$" should read --$L^1$-M-$L^2_b$--.

Signed and Sealed this

Eighteenth Day of August, 1998

Attest:

BRUCE LEHMAN

Attesting Officer

*Commissioner of Patents and Trademarks*